US006620805B1

(12) United States Patent
Takle et al.

(10) Patent No.: US 6,620,805 B1
(45) Date of Patent: Sep. 16, 2003

(54) DELIVERY OF NUCLEIC ACIDS BY PORPHYRINS

(75) Inventors: Garry B. Takle, New York, NY (US); Shaji T. George, New York, NY (US)

(73) Assignees: Yale University, New Haven, CT (US); Sirna Therapeutics, Inc., Boulder, CO (US)

( * ) Notice: Subject to any disclaimer, the term of this patent is extended or adjusted under 35 U.S.C. 154(b) by 1381 days.

(21) Appl. No.: 08/616,141

(22) Filed: Mar. 14, 1996

(51) Int. Cl.[7] .................. A01N 55/02; A61K 31/555
(52) U.S. Cl. .................. 514/185; 514/410; 514/44; 536/23.72
(58) Field of Search ................ 514/185, 410, 514/44; 536/23.72

(56) References Cited

U.S. PATENT DOCUMENTS

| 4,104,466 A | 8/1978 | Tsuchida et al. ............ 542/433 |
| 4,981,957 A | 1/1991 | Lebleu et al. ................. 536/27 |
| 5,166,320 A | 11/1992 | Wu et al. ..................... 530/395 |
| 5,192,788 A | * 3/1993 | Dixon et al. ................. 514/410 |
| 5,225,337 A | 7/1993 | Robertson et al. ............ 435/91 |
| 5,236,914 A | 8/1993 | Meunier et al. |

FOREIGN PATENT DOCUMENTS

| EP | 321021 A2 | 6/1989 |
| FR | 2 697 254 A | 4/1994 |
| GB | 2 146 525 A | 4/1985 |
| WO | WO 88/04300 | 6/1988 |
| WO | WO 89/05852 | 6/1989 |
| WO | WO 91/04324 | 4/1991 |
| WO | WO 93/01286 | 1/1993 |
| WO | WO 95/23225 | 8/1995 |
| WO | WO 95/27480 | 10/1995 |
| WO | WO 95/32739 | 12/1995 |
| WO | WO 95/33463 | 12/1995 |
| WO | WO 96/09315 | 3/1996 |

OTHER PUBLICATIONS

Smith & Morgan, "Hemopexin–Mediated Heme Transport To The Liver", Evidence For A Heme Binding Protein In Liver Plasma Membranes, *J. Biol. Chem.*, 260:8325–8329 (1985).
Smith, et al., "Methyl Deuteration Reactions In Vinylporphyrins: Protoporphyrins IX, III, And XIII", *J. Org. Chem.* 51:666–671 (1986).
Smith & Calvaleiro, "Protoporphyrin–IX: Some Useful Substituent Manipulations", *Heterocycles*, 26(7):1947–1963 (1987).
Spaltro & Methmanus, "The Synthesis And Characterization Of The Manganese (III) Chloride Protoporphyrin IX–Poly (Alpha–Amino Acid) Conjugates", (1988).
Pieken, et al., "Kinetic Characterization Of Ribonuclease–Resistant 2'–Modified Hammerhead Ribozymes", *Science*, 253:314–317 (1991).

Pispisa, et al., "Photophysical Behavior Of Poly(I–Lysine) Carrying Porphyrin And Naphthyl Chromophores", *Biopolymers*, 34:435–442 (1994).
R.R.C. New (ed.) "Liposomes: A Practical Approach", IRL Press, Oxford, 179–180 (1992).
Rossi, et al., "Exploring The Use Of Antisense, Enzymatic RNA Molecules (Ribozymes) As Therapeutic Agents", *Antisense Res. Dev.*, 1:285–288 (1991).
Sari, et al., "Cationic Porphyrin–DNA Interactions: Importance Of The Number And Position Of THe Charges", *Biochemical Pharmacologhy*, 37(9):1861–1862 (1988).
Sarin, et al., "Inhibition Of Acquired Immunodeficiency Syndrome Virus By Oligodeoxynucleoside Methyphosphonates", *Proc. Natl. Acad. Sci. USA*, 85:7448–7794 (1989).
Sells, et al., "Production Of Hepatitis B Virus Particles In HepG2 Cells Transfected With Cloned Hepatitis B Virus DNA", *Proc. Natl. Acad. Sci. USA*, 84:1005–1009 (1987).
Shaw, et al., "Modified Deoxyolidonucleotides Stable To exonuclease Degradation In Serum", *Nucleic Acids Res,* 19:747–750 (1991).
Sinclair, et al., "Effect Of Serum Proteins On Heme Uptake And Metabolism In Primary Cultures Of Liver Cells", *Biochem. J.*, 256:159–165 (1988).
Smith & Minnetian, "Cyclizations Of 1',8'–Dimethyl–a, c–biladience Salts To Give Porphyrins: A Study With Various Oxidizing Agents", *J. Chem. Soc., Perkin Trans I,* 277–280 (1986).
Smith & Morgan, "Hemopexin–Mediated Heme Uptake By Liver", *J. Biol. Chem.*, 259:12049–12053 (1984).
Adler, et al., "A Simplified Synthesis For Meso–Tetraphenylporphin", *J. Org. Chem.*, 32:476 (1967).
Adler, and Varadi, "Compounds Of Biological Interest", *Inorg. Syn.*, 16:213–220 (1976).
Aft, and Mueller, "Hemin–Mediated DNA Strand Scission", *J. Biol. Chem.*, 258:12069–12072 (1993).
Agrawal, et al., "Oligodeoxynucleoside Phpsphoramidates And Phosphorothioates As Inhibitors Of Human Immunodeficiency Virus", *Proc. Natl. Acad. Sci. USA*, 85:7079–7083 (1988).

(List continued on next page.)

*Primary Examiner*—Brenda Brumback
(74) *Attorney, Agent, or Firm*—Holland & Knight LLP

(57) ABSTRACT

Efficient methods and compositions are provided for the targeted delivery of effective concentrations of compounds, including nucleic acid molecules and oligonucleotides such as EGSs, ribozymes and antisense, proteins, peptides, carbohydrate, and synthetic organic and inorganic molecules, or combinations thereof, to cells, especially hepatocytes. In the preferred embodiment, the compound is an negatively charged oligonucleotide which binds in a stoichiometric ratio to a water soluble, positively charged macrocycle such as a porphyrin, which targets and protects the oligonucleotide. The porphyrin protects the compound to be delivered and delivers the compound preferentially to certain cells and tissue types. In another embodiment, the porphyrin has anti-human hepatitis virus activity, when administered alone, which is significantly enhanced when in combination with an antiviral compound, especially an oligonucleotide.

31 Claims, 6 Drawing Sheets

OTHER PUBLICATIONS

Altman, "RNA Enzyme–Directed Gene Therapy", *Proc. Natl. Acad. Sci. USA,* 90:10898–10900 (1993).

Buchler, "The Porphyrins", Dolphin, Ed., Chap 10, 389–483 (Academic Press: New York, 1978).

Cannon, et al., "Kinetics Of The Interaction Of Hemin Liposomes With Heme Binding Proteins", *Biochem.,* 23:3715–3721 (1984).

Cannon, "Pharmaceutics And Drug Delivery Aspects Of Heme And Porphyrin Therapy", *J. Pharm. Sciences,* 82(5):435–445 (1993).

Carvlin & Fiel, "Intercalative And Non–Intercalative Binding Of Large Cationic Porphyrin Lligands To Calf Thymus DNA", *Nuc Ac. Res.,* 11:6121–6139 (1983).

Carvlin, et al., "Circular Dichrosim Spectroscopy Of A Cationic Porphyrin Bound To DNA", *Biochem. Biophysical Res. Comm.,* 108(1):66–73 (1982).

Cech, "Self–Splicing Of Group I Introns", *Annu. Rev. Biochem.,* 59:543–568, (1990).

Chowdhury, et al., "Fate Of DNA Targeted To The Liver by Asialoglycoprotein Receptor–Mediated Endocytosis In Vivo", *J. Biol. Chem.,* 268(15):11265–11271 (1993).

Clarenc, et al., "Delivery of Antisense Oligonucleotides By Poly(L–lysine) Conjugation And Liposome Encapsulation", *Anti–Cancer Drug Design,* 8(1):81–94 (1993).

Doan, et al., "Sequence–Targeted Chemical Modifications Of Nucleic Acids By Complementary Oligonucleotides Covalently Linked To Porphyrins", *Nucleic Acids Research,* 15(21):8643–8658 (1987).

Dougherty & Pasternack, "Base Pair Selectivity In The Binding Of Copper (II) Tetrakis (4–N–methylpyridyl) Porphine To Polynucleotides Under Closely Packed Conditions", *Biophysical Chem.,* 44:11–19 (1992).

Dyer & Herzog, "Isolation Of Intact Nuclei For Nuclear Extract Preparation From a Fragile B–lymphocyte Cell Line", *Biotechniques,* 19:192–195 (1995).

Felgner, et al., "Cationic Liposome–Mediated Transfection", *Nature,* 337:387–388 (1989).

Felgner, "Particulate Systems and Polymers for In Vitro and In Vivo Delivery of Polynucleotides", *Advanced Drug Delivery Reviews,* 5:163–187 (1990).

Felgner, et al., "Lipofection: A Highly Efficient, Lipid–Mediated DNA–Transfection Procedure", *Proc. Natl. Acad. Sci. USA,* 84:7413–7147 (1987).

Forster & Altman, "Similar Cage–Shaped Structures For The RNA Components Of All Ribonuclease P And Ribonuclease MRP Enzymes", *Cell,* 62:407–409 (1990).

Frolova, et al., "Kinetic Study Of The Addressed Modification By Hemin Derivatives Of Oligonucleotides", *Biochimie,* 75:5–12 (1993).

Furhop, et al., In: Porphyrines and Metalloporphyrins, (K.M. Smith, Ed.) (Elsevier, Amsterdam), 804–807 (1975).

Galbraith, et al., "Heme Binding To Murine Erythroleukemia Cells", *J. Biol Chem.,* 260:12198–12202 (1985).

Galbraith, "Heme Binding To HepG2 Human Hepatoma Cells", *J. Hepatol.,* 10:305–301 (1990).

Gibbs, et al., "Self–Assembly Of Porphyrins On Nucleic Acid Templates", *Biochem. Biophys. Res. Com.,* 157:350–358 (1988).

Gibbs & Pasternack, "Interactions Of Porphyrins And Metalloporphyrins With Nucleic Acids", *Seminars in Hematology,* 26(2):77–85 (1989).

Gibbs, et al., "Interactions Of Porphyrines With Purified DNA And More Highly Organized", *J. Inorganic Biochem.,* 32:39–65 (1988).

Gonzalez & Weedon, "Preparation And Properties Of A Linked Porphyrin–Cyclodextin", *Can. J. Chem.* 63:602–608 (1985).

Grigoriey, et al., "A Triple Helix–Forming Oligonucleotide–Intercalator Conjugate Acts As A Transcriptional Repressor Via Inhibition Of NF κB Binding To Interleukin Receptor", *J. Biol. Chem.,* 267:3389–3395 (1992).

Guerrier–Takada, et al., "The RNA Moiety Of Ribonuclease P Is The Catalytic Subunit Of The Enzyme", *Cell,* 35:849–857 (1983).

Heidenreich & Eckstain, "Hammerhead Ribozyme–Mediated Cleavage Of The Long Terminal Repeat RNA Of Human Immunodeficiency Virus Type 1", *J. Biol. Chem,* 267:1904–1909 (1992).

Itakura, et al., "Synthesis And Use Of Synthetic Oligonucleotides", *Ann. Rev. Biochem.,* 53:323–356 (1984).

Kim, et al., "Preparation of Multivesicular Liposomes", *Biochimica et Biophysica Acta,* 728:339–348 (1983).

Korba & Gerin, "Use Of A Standardized Cell Culture Assay To Assess Activities Of Nucleoside Analogs Against Hepatitis B Virus Replication", *Antiviral Research,* 19:55–70 (1992).

Langlois, et al., "Biological Activities Of Phthalocyanines—IV. Type II Sensitized Photoxidation Of L–tryptophan And Cholesterol By Sulfonated Metallo Phthalocyanines", *Photochem. Photobiol.,* 44:117–123 (1986).

Larock, "Comprehensive Organic Transformation", *VCH,* New York, 966–972 (1989).

Lavallee, "Complexation And Demetalation Reactions Of Porphyrins", *Comments Inorg. Chem.,* 5:155–174 (1986).

Lavallee, "Kinetics And Mechanisms Of Metalloporphyrin Reactions", *Coord. Chem. Rev.* 61:55–96 (1985).

Leclerc, et al., "A Three Dimensional Model Of The Rev–Binding Element Of HIV–1 Derived From Analysis Of Aptamers", *Nature Struct. Biol.,* 1:293–300 (1994).

Lee, et al., "Recognition of Liposomes by Cells: In Vitro Binding and Endocytosis Mediated by Specific Lipid Headgroups and Surface Charge Density", *Biochimica et Biophysica Acta,* 1103:185–197 (1992).

Leonetti, et al., "Antibody–targeted Liposomes Containing Oligodeoxyribonucleotides Complementary to Viral RNA Selectively Inhibit Viral Replication", *Proc. Natl. Acad. Sci. USA,* 87:2448–2451 (1990).

Leserman, et al., "Targeted Liposomes and Intracellular Delivery of Macromolecules", *Horizons in Membrane Biotechnology,* 95–102 (1990).

Leventis & Silvius, "Interactions Of Mammalian Cells With Lipid Dispersion Containing Novel Metabolisable Cationic Amphiphiles", *Biochim. Biophys. Acta,* 1023:124–132 (1990).

Lindsey, et al., "Rothemund And Adler–Longo Reactions Revisited: Synthesis Of Tetraphenylporphyrins Under Equilibrium Conditions", *J. Org. Chem.* 52:827–836 (1987).

Lisiewicz, et al., Specific Inhibition of Human Immunodeficiency Virus Type 1 Replication By Antisense Oligonucleotides: An in vitro Model For Treatment, *Proc. Natl. Acad. Sci. USA,* 89:11209–11213 (1992).

Liu, et al., "Role Liposome Size and RES Blockade in Controlling Biodistribution and Tumor Uptake of $GM_1$–containing Liposomes", *Biochimica et Biophysica Acta,* 1104:95–101 (1992).

Lu, et al., "Drug Blinding By Branched DNA: Selective Interaction Of Tetrapyridyl Porphyrins With An Immobile Junction", *Biochemistry*, 29:1614–1624 (1990).

Machy, et al., "Interferon Sensitive and Insensitive MHC Variants of a Murine Thymoma Differentially Resistant to Methotrexate–Containing Antibody–Directed Liposomes and Immunotoxin", *J. Immunology*, 136(8):3110–3115 (1986).

Machy, et al., "Elimination or Rescue of Cells in Culture by Specifically Targeted Liposomes Containing Methotrexate or Formyl–Tetrahydrofolate", *EMBO Journal*, 3(9):1971–1977 (1984).

Magda, "Site–Specific Hydrolysis Of RNA By Europium(III) Texaphyrin Conjugated To A Synthetic Oligodeoxyribonucleotide",*J. Am. Chem. Soc.*, 116:7439–7440 (1994).

Maher, et al., "Inhibition Of DNA Binding Proteins By Oligonucleotide–Directed Triple Helix Formation",*Science*, 245:725–730 (1989).

Milhaud, P.G., et al., "Antibody Targeted Liposomes Containing Poly(rl)•poly(rC) Exert a Specific Antiviral and Toxic Effect on Cells Primed with Interferons α/β or Y", *Biochimica et Biophysica Acta*, 987:15–20 (1989).

Milhaud, et al., "Free and Liposome–Encapsulated Double–Stranded RNAs as Inducers of Interferon, Interleukin–6, and Cellular Toxicity", *J. of Interferon Res.*, 11(1):261–265 (1991).

Milligan, et al., "Oligoribonucleotide Synthesis Using T7 RNA Polymerase And Synthetic DNA Templates", *Nucl Acids Res.*, 15:8783 (1987.

Momenteau, et al., "Both–Faces Hindered Porphyrins, Part 4, Synthesis Of Functionalized Basket–handle Porphyrins Designed For A Strict Intramolecular Axial Ligation In Superstructured Complexes",*J. Chem. Soc., Perkin Trans. I*, 283–295 (1988).

Morgan & Dolphin, "Synthesis And Structure Of Biomimetic Porphyrins", *Struct. Bonding* (Berlin), 64 (Met. Complexes Tetrapyrrole Ligands I), 115–203 (1987).

Morgan, & Dolphin, "Syntheisi Of Hydrocarbon–Strapped Porphyrine Containing Quinone And Phenolic Groups", *J. Org. Chem.* 52:5364–5374 (1987).

Narang, et al., "Chemical Synthesis Of Deoxyoligonucleotides By The Modified Triester Method", *Methods Enzymol.*, 65:610–620 (1980).

Noé, et al., "Inhibition of Cell Proliferation with Antibody–Targeted Liposomes Containing Methotrexate–Y–Dimyristoylphosphatidylethanolamine", *Biochimica et Biophysica Acta*, 946:253–260 (1988).

Offensperger, et al., "In Vivo Inhibition Of Duck Hepatitis B Virus Replication And Gene Expression By Phosphorothioate Modified Antisense Oligodeoxynucleotides", *EMBO J.*, 12:1257–1262 (1993).

Orson, et al., "Oligonucleotide Inhibiton Of IL2Rα mRNA Transcription by Promoter Region Collinear Triplex Formation In Lymphocytes", *Nucl. Acids Res.*, 19:3435–3441 (1991).

Ortigao, et al., "Solid–Phase Introduction And Intracellular Photoinduced Reaction Of a Water–Soluble Meso–tetracarboxyporphine Conjugated To An Antisesne Oligodeoxyribonucleotide", *Biochimie.*, 75:29–34 (1993).

Oseroff, et al., "Antibody–Targeted Photolysis: Selective Photodestructio Of Human T–Cell Leukemia Cells Using Monoclonal Antibody–Chlorin",*Proc. Natl. Acad. Sci. USA*, 83:8744–8748 (1986).

Pace, et al., "A Ribozyme Which Discriminates in vitro Between PML/RARa, The t(15:17)–Associated Fusion RNA Of Acute Promyelocytic Leukaemia, And PML And RARa, The Transcripts From The Nonrearranged Alleles", *Cancer Research*, 54:6365–6369 (1994).

Paolella, et al., "Nuclease Resistant Ribozymes With High Catalytic Activity", *EMBO J.*, 11:1913–1919 (1992).

Pasternack, et al., "The Influence Of Ionic Strength On The Binding Of A Water–Soluble Porphyrin To Nucleic Acids", *Nuc. Acids Res.*, 14:5919–5931 (1986).

Spikes, "Phthalocyanines As Photosensitizers In Biological Systems And For The Photodynamic Therapy Of Tumors", *Photochem. Photobiol.*, 43:691–699 (1986).

Suzuki, et al., "CD4 and CD7 Molecules as Targets for Drug Delivery from Antibody Bearing Liposomes", *Exp. Cell Res.*, 193(1):112–119 (1991).

Symons, "Small Catalytic RNAs", *Annu. Rev. Biochem.*, 61:641–671 (1992).

Thierry, et al., "Multidrug Resistance in Chinese Hamster Cells: Effect of Liposome–Encapsulated Doxorubicin", *Cancer Communications*, 1(5):311–316 (1989).

Thierry, A.R., et al., "Overcoming Multidrug Resistance in Human Tumor Cells Using Free and Liposomally Encapsulated Antisense Oligodeoxynucleotides", *Biochem. Biophys. Res. Comm.*, 190(3):952–962 (1993).

Thierry, A.R., et al., "Intracellular Availability of Unmodified, Phosphorothioated and Liposomally Encapsulated Oligodeoxynucleotides for Antisense Activity", Nuc. Ac. Res., 20(21):5691–5698 (1992).

Tipping, et al., "Interactions Of Small Molecules With Phospholipid Bilayers", *Biochem. J.*, 180:327–337 (1979).

Truneh, et al., "A Calmodulin Antagonist Increases the Apparent Rate of Endocytosis of Liposomes Bound to MHC Molecules Via Monoclonal Antibodies", *Exp. Cell Res.*, 155:50–63 (1984).

Tsuchida, et al., "Cooperative Reactions Of Poly–l–Lysine–Heme Complex With Molecular Oxygen, Carbon Monoxide, Or Cyanide Ion", *Biochimica Et Biophysica Acta: Protein Structure*, 427:p43 (1976).

Ushakova, et al., "Preparation Of Liposomal Forms Of Hemin Hydrophobic Derivatives", *Biotech.*, 1128–1132 (1988) Abstract.

Villenueva & Jori, "Pharmokinetic And Tumor–Photosensitising Properties Of The Porphyrin Meso–ttra (4N–methylpyridyl) Porphine", *Cancer Lett.*, 73:59–64 (1993).

Wang, et al., "Highly Efficient DNA Delivery Mediated by pH–Sensitive Immunoliposomes",*Biochem.*, 28:9508–9514 (1989).

Wu & Wu, "Receptor–Mediated in vitro Gene Transformation By A Soluble DNA Carrier System", *J. Biol. Chem.*, 262:4429–4432 (1986).

Yamagishi & Watanabe, "Electric Dichroism Studies On Ferriheme– And Ferroheme–Poly(L–lysine) Complexes At pH 9–12", *Biopolymers*, 21:89–100 (1982).

Yu, et al., "A Hairpin Ribozyme Inhibits Expression Of Diverse Strains Of Human Immunodeficiency Virus Type 1", *Proc. Natl. Acad. Sci. USA*, 90:6340–6344 (1993).

Yuan, et al., "Targeted Cleavage Of mRNA By Human RNase P", *Proc. Natl. Acad. Sci. USA*, 89:8006–8010 (1992).

Anneheim–Herbelin, et al., "Porphyrin–Netropsin: A Potential Ligand of DNA," *Tetrahedron Lett.*, 34(45), 7263–7266 (1993).

Bigey, et al., "DNA Binding and Cleavage by a Cationic Manganese Porphyrin—Peptide Nucleic Acid Conjugate," *Bioconjugate Chem.*, 8(3), 267–270 (1997).

Kluetsch, et al., "Metal Porphyrin/Oligonucleotide Conjugates: Synthesis and Use as Chemiluminescent DNA Probes," *Chemical Abstracts*, 125(23), Abstract No. 296435 (1996).

Mestre, et al., "Structure/Nuclease Activity Relationships of DNA Cleavers Based on Cationic Metalloporphyrin—Oligonucleotide Conjugates," *Biochemistry*, 35(28), 9140–9149 (1996).

Pitié, et al., "Selective Cleavage of a 35–mer Single–Stranded DNA Containing the Initiation Codon of the TAT Gene of HIV–1 by a Tailored Cationic Manganese Porphyrin," *Angew. Chem.*, 32(4), 557–559 (1993).

Pitié, et al., "Cleavage of Double–Stranded DNA by Manganese Tris (Methylpyridiniumyl) Porphyrin Linked to 3'–Spermine Oligonucleotides," *Chemical Abstracts*, 125(25), Abstract No. 316386 (1996).

Schubert, et al., "Anionic Manganese meso—Tetraphenyl Porphine/Oligonucleotide Conjugates—Synthesis and Utilization in Chemiluminescent DNA—Probe Detection," *Nucleosides & Nucleotides*, 16(3), 277–289 (1997).

\* cited by examiner

DELIVERY OF NUCLEIC ACIDS BY PORPHYRINS

BACKGROUND OF THE INVENTION

The present invention relates generally to delivery of compounds with a net negative charge, especially oligonucleotides, to specific cell types, and is in particular a means of using positively-charged porphyrins and other macrocyclic compounds with positive charges that can stack along oligonucleic acid backbones to stabilize and promote uptake into cells of the oligonucleotides or other negatively charged compounds. The present invention is also a method for treating viral diseases, especially hepatitis B and C.

Targeted drug delivery improves the therapeutic index of numerous drugs, reduces potential drug cost and may increase tissue half life. Although drugs can be encapsulated in tablets or capsules for oral delivery, encapsulation into more sophisticated vehicles is required for targeted delivery and for delivery of molecules such as therapeutic oligonucleotides and gene therapy reagents, which are extremely sensitive to the presence of nucleases in the body.

Many different systems have been proposed for targeted drug delivery. The most commonly used method has been to covalently attach antibodies to the surface of microparticulate carriers.

Delivery of short nucleic acids to the liver is a crucial step in their use as genetic therapeutics in hepatic illness. In hepatitis caused by the human hepatitis viruses, the hepatocytes are the sites of intracellular viral replication and are thus the target cells for antiviral therapies. Receptor-mediated uptake of oligonucleotides into hepatocytes has been used as a strategy for the specific delivery, as described by Wu and Wu (1986) Receptor-mediated in vitro gene transformation by a soluble DNA carrier system *J. Biol. Chem.* 262, 4429–4432. Receptors such as the asialoglycoprotein receptor and the heme receptor (Galbraith, R. A. (1990) Heme binding to HepG2 human hepatoma cells. *J. Hepatol.*, 10, 305–310) have been successfully targeted. Immunoliposomes, i.e., liposomes bearing antibodies have also been used to direct drug delivery. However, the coupling of polypeptide ligands to the surface of liposomes presents a number of problems, mainly due to the fact that such ligands contain multiple reactive groups. Carbodiimide-mediated peptide bond formation between complex ligand molecules such as carbohydrates or polypeptides and reactive groups on the outer surface of liposomes can result in considerable intramolecular coupling and intermolecular coupling between ligand molecules, in addition to the desired intermolecular coupling between liposome and ligand. Complex ligands are also more likely to be immunogenic and could therefore evoke an immune reaction resulting in rapid clearance by the immune system of the body.

It is therefore an object of the present invention to provide a means for stabilizing and delivering nucleic acids.

It is a further object of the present invention to provide compositions for efficient, simple and reliable delivery to specific cell types, especially of nucleic acid-type molecules, such as external guide sequences for RNase P, antisense oligonucleotides and ribozymes.

It is another object of the present invention to provide methods and compositions for treating hepatotrophic viruses; especially human hepatitis B and C viruses.

SUMMARY OF THE INVENTION

Efficient methods and compositions are provided for delivery of effective concentrations of compounds, including nucleic acid molecules and oligonucleotides such as ribozymes, external guide sequences for RNase P, and antisense oligonucleotides, proteins, peptides carbohydrate, and other synthetic organic and inorganic molecules having biological activity or useful as a diagnostic, or combinations thereof, to cells, especially hepatocytes and tumor cells, which preferentially bind prophyrins or phthalocyanins (referred to jointly herein as "porphyrins" unless otherwise stated) or other macrocylic compounds. The system is extremely simple, since the two principle components are a porphyrin having a net overall positive charge, as defined in more detail below, and the compound to be delivered, wherein the compound has a net overall negative charge. The porphyrin binds the compound to be delivered and selectively targets the compound to cells preferentially binding the porphyrin.

As demonstrated by the examples, in a preferred embodiment the compound is an oligonucleotide which binds to the porphyrin in a stoichiometric ratio, and greatly enhances uptake by cells. The examples demonstrate delivery to hepatocytes, lack of side effects in animals, inhibition of viral replication due to both the oligonucleotide and porphyrins, with a significant enhancement of the anti-viral activity due to the combination of oligonucleotide and porphyrin. The combination has utility in inhibition of viral replication in cells, as well as other therapeutic applications, as well as in research and diagnostic applications.

Also disclosed is the use of the porphyrins alone as anti-human hepatitis B agents, having anti-viral activity in the absence of the anti-viral oligonucleotide.

BRIEF DESCRIPTION OF THE DRAWINGS

FIG. 3a, 4 h; FIG. 3b, 24 h.

FIG. 4 is a graph of the amount of cell-associated oligo (micrograms) delivered to NB4 cells versus micrograms TMP.

DETAILED DESCRIPTION OF THE INVENTION

Figure 1:
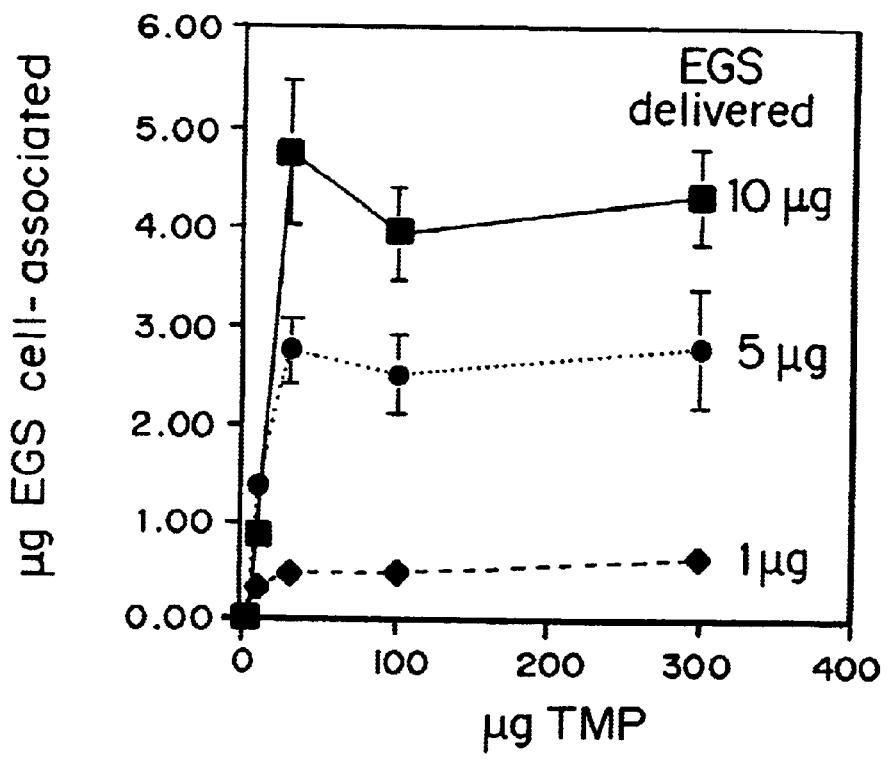
FIG. 1 is a graph of the amount of EGS (micrograms) associated with human hepatoma-cells (HepG2 2.2.15 cells). Cells were plated out onto 96-well plates at $10^4$ cells per well, and left for 3 days until approximately 90% confluent. One, 5 or 10 μg of oligo A were complexed with 0–300 μg of TMP in 40 μl 150 mM NaCl and delivered to the cells.

Methods and compositions for the delivery of compounds, including nucleic acid molecules and oligonucleotides such as ribozymes, external guide sequences for RNase P, and antisense oligonucleotides, proteins, peptides carbohydrate, and other synthetic organic and inorganic molecules having biological activity or useful as a diagnostic, or combinations thereof, and non-therapeutic compounds, to specific cells-using macrocyclic compounds are provided. In the preferred embodiments, the macrocyclic compounds are porphyrins or phthalocyanins; in the most preferred embodiment, the porphyrins are water soluble. The compound to be delivered has a net overall negative charge; the macrocyclic compound has a net overall positive charge under physiological conditions, i.e., pH of approximately 7.0–7.5, more typically 7.2 to 7.4. As a result, the compound to be delivered is ionically bound to the macrocyclic compound until it and the bound nucleic acids are internalized in the targeted cells.

The stabilized and/or targeted compounds offer an advantage in that, since they are preferentially bound and taken up by cells, the effective concentration of the compound to be delivered, especially oligonucleotide, is significantly reduced. Such targeted delivery may also reduce systemic side effects that can arise from using relatively high drug concentrations in non-targeted delivery methods.

The major issues that are important in the delivery of nucleic acids are the following:

Protection—does the delivery system prevent the nucleic acid drug from being degraded? This problem can be overcome to some extent by designing synthetic nucleic acid molecules that are chemically modified and resistant to nuclease degradation. Chemical modification, however, can compromise biological activity.

Concentration—delivery of high enough concentrations of nucleic acid to ensure a biological effect—for different situations different amounts of therapeutic may be needed and the delivery system can be tailored to deliver specific amounts to certain cells.

Specific delivery—does the delivery system deliver nucleic acids to the right target? And if not, does a systemic delivery of drug lead to unwanted side-effects.

Delivery to the correct intracellular target site—it may not be sufficient to deliver nucleic acids to target cells to apparently effective concentrations if the therapeutic remains concentrated and trapped in intracellular compartments and unavailable for activity.

Toxicity—the delivery system cannot increase the toxicity of the nucleic acid plus delivery vehicle complex as a whole.

Complexity—the simpler the delivery system, the fewer the molecular components, the easier it is to fully characterise. Simplicity of preparation and ease of use are also significant factors in the development of delivery systems.

As demonstrated herein, this system meets all of these requirements for delivery of oligonucleotides.

I. Porphyrins, Phthalocyanins and other Macrocycles

The photochemistry and photophysics of porphyrins, metalloporphyrins, and phthalocyanines have been studied in detail. Processes observed include loss of an axial ligand, energy transfer, electron transfer, formation of singlet oxygen, phosphorescence and fluorescence. The photoprocesses observed in each system depend greatly on the central ligand, normally a metal (2H for porphyrin), the oxidation state of the metal and the axial ligand bound to the metal. A weaker dependence of the photophysical properties on the nature of the macrocycle is observed. Porphyrins and phthalocyanines have been reported to have a variety of other biological activities, including some anti-HIV activity. However, relatively little has been done with them with respect to in vivo clinical applications other than in photodynamic tumor therapy.

Porphyrins are macrocycle compounds with bridges of one carbon atom or one nitrogen atom respectively, joining the pyrroles to form the characteristic tetrapyrrole ring structure. There are many different classes of porphyrin-like compounds. The term porphyrins will be used herein to refer to porphyrins, phthalocyanines, chlorins, metallo derivatives thereof, and other porphyrin-like compounds or macrocycles possessing antiviral activity or which are postively charged and therefore capable of binding to oligonucleotides and other negatively charged compounds to be delivered.

Those porphyrins and phthalocyanins that are useful in the methods and compositions described herein for targeted delivery of compounds have an overall net negative charge; are water soluble, defined herein as soluble to at least a level of 20 mg/ml saline, and have a net overall positive charge, for example, compounds containing a quaternary methyl amine groups synthesized by interaction of a tertiary amine with a nucleophile.

In the preferred embodiment for anti-viral treatment, the porphyrin is water soluble but the positive charge is not essential. In the most preferred embodiment for anti-viral treatment, the porphyrin has low toxicity and anti-viral activity in nanomolar concentrations. The most preferred anti-viral activity is anti-human hepatitis virus activity, especially anti-human hepatitis B and/or C.

Some porphyrins are isolated from nature, for example, protoporphyrin IX, which is the organic portion of hemin. Many derivatives of natural porphyrins are known (see, for example Smith and Cavaleiro, "Protoporphyrin-IX: Some Useful Substituent Manipulations", *Heterocycles,* 26, 1947–1963, (1986), the teachings of which are incorporated herein). Many other porphyrins and phthalocyanines are synthesized in the laboratory. These include those made via the condensation of aldehydes and pyrroles, such as tetraphenylporphyrin. They also include compounds built up from smaller organic fragments.

Porphyrin-like compounds can have one or more substituents, and combinations of one or more different substituents. The substituents can be symmetrically or asymmetrically located. The substituents, as well as the overall structure, can be neutral, positively charged or negatively charged. Charged structures have counterions, and many counterions and combinations of counterions are possible.

Porphyrins can be covalently attached to other molecules, for example, cyclodextrins (Gonzalez, M. C.; Weedon, A. C. *Can. J. Chem.* 63, 602–608 (1985)). They can have an attached molecular superstructure. The conjugation of the ring can be altered by addition of one or more substituents. In addition, metals can be inserted into the tetrapyrrole ring. Examples of such metals include, but are not limited to, Fe, Co, Zn, Mo, Ti, Mn, Cr, Ni, Mg, Cu, Tl, In, Ru, V and Au. Additional ligands can be attached to the metal.

Both natural and synthetic porphyrins, phthalocyanines and metallo derivatives can be used. Examples include 5,10-Diphenyl-15,20-di(N-methyl-3-pyridyl)-porphyrin; 5,10-Diphenyl-15,20-di(N-methyl-4-pyridyl)-porphyrin; 5,15-Diphenyl-10,20-di(N-methyl-3-pyridyl)-porphyrin; Hemin; Protoporphyrin; Tetra-(N-methyl-4-pyridyl)-porphyrin; Meso-tetraphenylporphine; Protoporphyrin IX dimethyl ester; Tetra-(4-carboxyphenyl)-porphyrin; Tetra-(4-methylphenyl)-porphyrin; Tetra-(3-methylphenyl)-porphyrin; Tetra-(4-hydroxyphenyl)-porphyrin; Fe(III)-tetraphenyl-porphyrin; Tetra-(4-chlorophenyl)-porphyrin; Fe(III)-tetra-(4-methylphenyl)-porphyrin; Fe(III)-tetra-(N-methyl-4-pyridyl)-porphyrin; Fe(III)-mu-oxo-dimer of tetraphenylporphyrin; nickel phthalocyanine tetrasulfonic acid; copper phthalocyanine 3,4',4",4'''-tetrasulfonic acid; and copper phthalocyanine.

Examples of synthetic porphyrins include 5,10-Diphenyl-15,20-di(N-methyl-3-pyridyl)-porphyrin Cl—, 5,10-Diphenyl-15,20-di(N-methyl-4-pyridyl)-porphyrin Cl—, 5-Diphenyl-10,20-di(N-methyl-4-pyridyl)-Cl—porphyrin Cl—, 5,15-Diphenyl-10,20-di(N-methyl-3-pyridyl)-porphyrin Cl—, Tetra-(N-methyl-4-pyridyl), porphyrin tosylate salt (TMPyP), Meso-tetraphenylporphine (TPP), Tetra-(4-carboxyphenyl)-porphyrin (TPP(4-$CO_2$H)$_4$), Tetra-(4-methylphenyl), porphyrin (TPP(4-Me)$_4$), Tetra-(3-methylphenyl)-porphyrin (TPP(3-Me)$_4$), Tetra-(4-hydroxyphenyl)-porphyrin (TPP(4-OH)$_4$), and Tetra-(4-chlorophenyl)-porphyrin (TPP(4-Cl)$_4$).

Examples of synthetic metalloporphyrins include Fe(III)-tetraphenylporphyrin chloride (FeTPPCl), Fe(III)-tetra-(4-methylphenyl)-porphyrin chloride (FeTPP) (4-Cl)$_4$, Fe(III)-tetra-(N-methyl-4-pyridyl)-porphyrin chloride (FeTMPyP), Fe(III)-mu-oxo-dimer of tetraphenyl-porphyrin ($\mu$-oxo-TPP), Cu(II)-5,10-diphenyl-15,20-di(N-methyl-4-pyridyl)-porphyrin (Cu-CP4), and Ni(II)-5,10-diphenyl-15,20-di(N-methyl-4-pyridyl)-porphyrin (Ni-CP4).

Examples of phthalocyanines include Copper phthalocyanine tetrasulfonic acid tetra-sodium salt (CuPHTHS$_4$), Nickel phthalocyanine tetrasulfonic acid (NiPHTHS$_4$), Copper phthalocyanine 3,4',4",4'''-tetrasulfonic acid (CuPHTHS$_4$) (3,4,4,4), Copper phthalocyanine (CuPHTH), Copper-4,4',4",4'''-tetra-aza-29H.

Protohemin can be obtained from Aldrich Chemical Co., Milwaukee, Wis. Fe(III) tetraphenylporphyrin derivatives were either purchased from Midcentury Chemicals or synthesized by pyrrole-benzaldehyde condensation in a propionic acid reflux, by the method of A. D. Adler, F. R. Longo, J. D. Finarelli, J. Goldmacher, J. Assour, and L. Korsakoff, *J. Org. Chem.*, 32, 476 (1967). Iron can be inserted using FeCl$_2$ in dimethylformamide, as taught by A. D. Adler, F. R. Longo, and V. Varadi, *Inorg. Syn.*, 16, 213–220 (1976). General synthetic references are Dolphin, D. Ed., "The Porphyrins", Vol. 6, Chap 3–10, pp. 290–339 (Academic Press: New York, 1979); Morgan, B., Dolphin, D. *Struct. Bonding* (Berlin), 64 (Met. Complexes Tetrapyrrole Ligands I), pp. 115–203 (1987); Smith, Kevin M.; Cavaleiro, Jose A. S. *Heterocycles*, 26(7), 1947–63 (1987).

Still other synthetic techniques include the methods of Lindsey, et al., *J. Org. Chem.* 52, 827–836 (1987); Momenteau, M.; Loock, B.; Huel, C.; Lhoste, J. M. *J. Chem. Soc., Perkin Trans. I*, 283 (1988); Morgan, B.; Dolphin, D. *J. Org. Chem.* 52, 5364–5374 (1987); Smith, K. M.; Parish, D. W.; Inouye, W. S. *J. Org. Chem.* 51, 666–671 (1986); and Smith, K. M.; Minnetian, O. M. *J. Chem. Soc., Perkin Trans. I*, 277–280 (1986). Other references to metal insertion include Buchler, J. E., "The Porphyrins", vol. 1, ch. 10, Dolphin, D., ed. (Academic Press, NY 1979); Lavallee, D. K. *Coord. Chem. Rev.* 61, 55–96 (1985); Lavallee, D. K. *Comments Inorg. Chem.* 5, 155–174 (1986).

Phthalocyanines can be synthesized by the condensation of phthalonitrile and its derivatives. Functionalization of the phthalocyanine ring system is readily achieved, using the method of Langlois, et al., "Biological activities of phthalocyanines—IV. Type II sensitized photoxidation of L-tryptophan and cholesterol by sulfonated metallo phthalocyanines." *Photochem. Photobiol.*, 44, 117–123, (1986), and Spikes, J. D. *Photochem. Photobiol.*, 43, 691–699, (1986).

Porphyrins and phthalocyanines may also be obtained from commercial sources including Aldrich Chemical Co., Milwaukee, Wis., Porphyrin Products, Logan, Utah, and Midcentury Chemicals, Posen, Ill.

Chlorins, another group of useful porphyrins, can be made using the method described by Oseroff, et al., *Proc. Natl. Acad. Sci. USA*, 83, 8744–8748 (1986).

Examples of natural porphyrins are Protoporphyrin, disodium salt (PPIX) and Protoporphyrin IX dimethyl ester (PPIXDME). Examples of natural metalloporphyrins include hemin, bovine, (chloroprotoporphyrin IX Fe(III)) (FePPIXCl).

Metalloporphyrins are organic compounds whose structure includes a porphyrin ring which contains in its center a prosthetic metal atom, such as iron or magnesium, held by four inwardly-facing nitrogen atoms. Metalloporphyrins have been found associated with a variety of proteins such as globin, myoglobin and cytochromes, and in pigment molecules, such as chlorophylls. Such proteins consist of the metalloporphyrin moiety and the remaining portion comprising the protein called the apoprotein.

Heme, the common metalloporphyrin found in hemoglobin and cytochromes, is synthesized in animal cells by the chelation of an atom of iron with protoporphyrin IX using ferrochelatase. In hemoglobin, the heme molecule confers a reversible oxygen-binding capacity, whereas in cytochromes heme functions in electron transfer. Heme is a planar molecule and is capable of intercalating into double-stranded DNA (Aft, R. L. and Mueller, G. C., *J. Biol. Chem.* (1983), 258, 12069–12072, (1993); Carvlin, M. J. et al. *Nucleic Acids Res.* 11, 6121–6139 (1983)) and within lipid bilayers (Cannon, J. B., et al., *Biochem.* 23, 3715–3721 (1984); Tipping, E., et al., *Biochem. J.* 180, 327–337 (1979)). Heme contains two carboxyl groups which can serve as sites for peptide bond formation with amino group-containing molecules. Heme is readily available as an inexpensive reagent in the form of heme chloride (hemin, Sigma Chemical Co., St. Louis, Mo.).

The degradation of hemoglobin is an essential function of the liver and spleen as part of the removal of senescent erythrocytes from the circulation. The apoprotein in hemoglobin, i.e., globin, is degraded to its constituent amino acids, and heme is initially degraded by heme oxygenase to biliverdin. Biliverdin is then reduced further to bilirubin by biliverdin reductase. There appears to be some disagreement about the mechanism of binding and uptake of heme by the liver during its metabolism. Some evidence suggests that heme is transported to the liver completed with carrier proteins such as hemopexin (Smith, A. and Morgan, W. T., *J. Biol. Chem.*, 259,12049–12053 (1984)), or albumin (Sinclair, P. R., et al., *Biochem. J.*, 256, 159–165 (1988)), while other data suggests that heme can bind directly to the hepatocyte membrane without the requirement for a carrier (Galbraith, R. A., *J. Hepatol.*, 10, 305–310 (1990)). Whether or not a carrier protein is involved in the binding of heme to the hepatocyte, a heme receptor has been identified on the plasma membrane of hepatocytes (Galbraith, R. A. (1990))

and other cell types (Galbraith, R. A., et al. *J. Biol Chem.*, 260, 12198–12202 (1985)), and this surface receptor binds heme specifically. The heme receptor is an integral membrane protein of apparent molecular weight 115 kilodaltons (kD) that may constitute up to 0.5% of the total liver membrane protein.

The nature of the protoporphyrin receptor(s) on the surface of cells is still unclear. A heme derivative that can be used instead of heme is an aminodiglyceride such as dioleoylphosphatidyl ethanolamine which contains a heme molecule attached to the ethanolamine residue, or other diglyceride with a heme group attached directly to the glycerol. These lipids can be included directly during the formation of liposomes.

The interaction of water soluble porphyrins with nucleic acids has been looked at by several workers as a method for investigating the higher structures of DNA and for helping to understand porphyrin drug:nucleic acid associations (Villenueva and Jori (1993) Pharmokinetic and tumor-photosensitising properties of the porphyrin meso-ttra(4N-methylpyridyl)porphine. *Cancer Lett.* 73, 59–64; Gibbs, et al. (1988) Interactions of porphyrins with purified DNA and more highly organised structures. *J. Inorg. Biochem.* 32, 39–65; Gibbs, et al. (1988) Self-assembly of porphyrins on nucleic acid templates. *Biochem. Biophys. Res. Comm.* 157, 350–358; Gibbs and Pasternack (1989) Interactions of porphyrins and metalloporphyrins with nucleic acids. *Seminars in Hematology*, 26, 77–85; Pasternack, et al. (1986) The influence of ionic strength on the binding of a water-soluble porphyrin to nucleic acids. *Nuc. Acids Res.* 14, 5919–5931; Carvlin and Fiel (1983) Intercalative and non-intercalative binding of large cationic porphyrin ligands to calf thymus DNA. *Nuc Ac. Res.* 11, 6121–6139). Water soluble porphyrins have been shown to be capable of crossing the nuclear membrane (Gibbs, et al. (1988)) and have well-documented effects on naked DNA and chromatin during phototherapy (Aft. and Mueller (1983) Hemin-mediated DNA strand scission. *J. Biol. Chem.* 258, 12069–12072). Porphyrins are well known to be tumor localisers and for this reason these water soluble cationic versions have attracted attention. Water soluble anionic porphyrins have been conjugated to oligonucleotides as a method for the site-specific cleavage of the target sequence photoinduced by the porphyrin after hybridisation (Ramalho Ortigao, et al. (1993) Solid-phase introduction and intracellular photoinduced reaction of a water-soluble meso-tetracarboxyporphine conjugated to an antisense oligodeoxyribonucleotide. *Biochimie* 75, 29–34). The porphyrin described in the latter work localises however to the cytoplasm, and exerts its effect only after lazer light has been passed through cells.

II. Compounds

Proteins, peptides, polysaccharides, synthetic organic molecules including nucleotide/nucleoside analogues, ("drugs"), oligonucleotides, and other biologically active compounds having a net negative charge can be delivered selectively using the porphyrins described above.

In the preferred embodiment, the compound is an oligonucleotide. Nucleotides analogs are preferred to nucleosides since they contain negatively charged phosphate groups and have no need for phosphorylation within cells for activation. Preferred oligonucleotides are in the range of between one up to 200 nucleotides.

As used herein, the term "oligonucleotides" includes any nucleic acid molecules, especially ribozymes, antisense oligonucleotides, aptamers, triplex molecules and antisense oligonucleotides. Examples of compounds falling within this group include DNA and RNA for transfection. Included within the group of ribozymes are external guide sequences for directing cleavage of a substrate RNA by RNase P. Nucleotide molecules may be RNA, DNA, or modified nucleic acid molecules including derivatives or modified nucleotides which enhance stability.

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

The development of nucleic acid therapeutics, described, for example, with reference to antisense by Lisziewicz, et al. (1992) Specific inhibition of human immunodeficiency virus type 1 replication by antisense oligonucleotides: An in vitro model for treatment. *Proc. Natl. Acad. Sci. USA*, 89, 11209–11213); gene therapies and external guide sequences for RNase P (EGSs) by Yuan, et al. (1992) Targeted cleavage of mRNA by human RNase P. *Proc. Natl. Acad. Sci. USA*, 89, 8006–8010; ribozymes by Pace, et al. (1994) A ribozyme which discriminates in vitro between PML/RARa, the t(15:17)-associated fusion RNA of acute promyelocytic leukaemia, and PML and RARa, the transcripts from the nonrearranged alleles. *Cancer research*, 54, 6365–6369; Yu, et al. (1993) A hairpin ribozyme inhibits expression of diverse strains of human immunodeficiency virus type 1. *Proc. Natl. Acad. Sci. USA*, 90, 6340–6344); triplex-forming oligonucleotides and aptamers by Leclerc, et al. (1994) A three dimensional model of the Rev-binding element of HIV-1 derived from analysis of aptamers. *Nature Struct. Biol.*, 1, 293–300, the teachings of all of which are specifically incorporated herein, for use as viable treatments for human disease depends on their correct delivery to effective levels in target cells.

The discovery of catalytic RNA, by Drs. Altman and Cech, who were awarded the Nobel prize in 1989, has generated much interest in commercial applications, particularly in therapeutics (Altman, *Proc. Natl. Acad. Sci. USA* 90:10898–10900 (1993); Symons, *Annu. Rev. Biochem.* 61:641–671 (1992); Rossi et al., *Antisense Res. Dev.*, 1:285–288 (1991); Cech, *Annu. Rev. Biochem.* 59:543–568, (1990)). Several classes of catalytic RNAs (ribozymes) have been described, including intron-derived ribozymes (WO 88/04300; see also, Cech, T., *Annu. Rev. Biochem.*, 59:543–568, (1990)), hammerhead ribozymes (WO 89/05852 and EP 321021 by GeneShears), axehead ribozymes (WO 91/04319 and WO 91/04324 by Innovir).

Another class of ribozymes include the RNA portion of an enzyme, RNase P, which is involved in the processing of transfer RNA (tRNA), a common cellular component of the protein synthesis machinery. Bacterial RNase P includes two components, a protein (C5) and an RNA (M1). Altman and coworkers demonstrated that the M1 RNA is capable of functioning just like the complete enzyme, showing that in Escherichia coli the RNA is essentially the catalytic component, (Guerrier-Takada et al., *Cell* 35:849–857 (1983)). In subsequent work, Dr. Altman and colleagues developed a method for converting virtually any RNA sequence into a substrate for bacterial RNAse P by using an external guide sequence (EGS), having at its 5' terminus at least seven nucleotides complementary to the nucleotides 3' to the cleavage site in the RNA to be cleaved and at its 5' terminus the nucleotides NCCA (N is any nucleotide) (WO 92/03566 and Forster and Altman, *Science* 238:407–409 (1990)). Using similar principles, EGS/RNAse P-directed cleavage of RNA has been developed for use in eukaryotic systems, (Yuan et al., *Proc. Natl. Acad. Sci. USA* 89:8006–8010 (1992)). As used herein, "external guide sequence" and "EGS" refer to any oligonucleotide that forms an active cleavage site for RNAse P in a target RNA. EGS molecules are synthetic oligonucleotides that bind to a target substrate to form a secondary and tertiary structure resembling the natural cleavage site of precursor tRNA for eukaryotic RNase P.

Exemplary EGS molecules have been constructed which are suitable for use in the treatment of viral disease. The specific targets were the hepatitis B virus, more particularly, the hepatitis B surface antigen (HBsAg) encoding and pregenomic RNA. Since HBsAg plays an essential role in viral suprastructure and infection, EGS-based therapeutics can be used to down-regulate hepatitis through cleavage of HBsAg mRNA. Preferred targeted sites within hepatitis B RNA, or other target RNAS, are regions of conserved sequence which appear in all forms of the target RNA. At least two preferred sites have been identified in the HBsAg encoding region of hepatitis B RNA and are targeted by EGS molecules having complementary nucleotide base sequences.

Methods to produce or synthesize oligonucleotides are now routine using automated nucleic acid synthesis, for example, using the cyanoethyl phosphoramidite method on a DNA model 392 synthesizer by Applied Biosystems, Inc. (Foster City, Calif.) or a Pharmacia Oligo Pilot (Pharmacia, Piscataway, N.J.). Other methods for synthesizing nucleic acid molecules are also available (see, for example, Ikuta et al., *Ann. Rev. Biochem.* 53:323–356 (1984) (phosphotriester and phosphite-triester methods); Narang et al., *Methods Enzymol.* 65:610–620 (1980) (phosphotriester method). Alternatively, oligonucleotides can be synthesized by transcribing DNA templates, for example, with T7 RNA polymerase (Milligan et al., *Nucl Acids Res.* 15:8783 (1987)). Oligonucleotides can also be synthesized in cells by transfecting a vector that encodes and expresses the oligonucleotides in the cells.

Chemical modifications can be made which greatly enhance the nuclease resistance of an oligonucleotide without compromising its biological function. For example, one or more of the bases can be replaced by 2' methoxy ribonucleotides, phosphorothioate deoxyribonucleotides, or phosphorothioate ribonucleotides using available nucleic acid synthesis methods (see, for example, Offensperger et. al., *EMBO J.*, 12:1257–1262 (1993); WO 93/01286 by Rosenberg et al., (synthesis of sulfurthioate oligonucleotides); Agrawal et al., *Proc. Natl. Acad. Sci. USA,*. 85:7079–7083 (1988); Sarin et al., *Proc. Natl. Acad. Sci. USA,* 85:7448–7794 (1989); Shaw et al., *Nucleic Acids Res,* 19:747–750 (1991) (synthesis of 3' exonuclease-resistant oligonucleotides containing 3' terminal phosphoroamidate modifications); incorporated herein by reference).

It is well documented in the current literature that degradation of oligonucleotide analogues is mainly attributable to 3'-exonucleases. Several studies have also demonstrated that various 3'-modifications can greatly decrease the nuclease susceptibility of these analogues. Thus, another method to reduce susceptibility to 3' exonucleases is introduction of a free amine to a 3' terminal hydroxyl group of the EGS molecule (see, for example, Orson et al., *Nucl. Acids Res.,* 19:3435–3441 (1991)). Another useful 3' terminal modification is to couple a thymine nucleotide to the 3' end of an EGS with a 3' to 3' linkage. Such a structure is referred to herein as 3'-3'-thymine nucleotide or T(3'-3'). Additional useful modifications include methylation of cytosine bases that may be present in the sequence, and covalent attachment of an intercalating agent, such as an acridine derivative, to a 5' terminal phosphate (for example, using a pentamethylene bridge), in order to reduce the susceptibility of a nucleic acid molecule to intracellular nucleases (see, for example, Maher et al., *Science,* 245:725–730 (1989); Grigoriev et al., *J. Biol. Chem.,* 267:3389–3395 (1992)).

Another class of chemical modifications is modification of the 2' OH group of a nucleotide's ribose moiety, which has been shown to be critical for the activity of the various intracellular and extracellular nucleases. Typical 2' modifications are the synthesis of 2'-O-Methyl oligonucleotides (Paolella et al., *EMBO J.,* 11:1913–1919, 1992) and 2'-fluoro and 2'-amino-oligonucleotides (Pieken, et al., *Science,* 253:314–317 (1991); Heidenreich and Eckstein, *J. Biol. Chem,* 267:1904–1909 (1992)). Portions of EGS molecules can also contain deoxyribonucleotides. Such substitutions improve nuclease resistance by eliminating the critical 2' OH group.

WO 95/23225 by Ribozyme Pharmaceuticals, Inc. describes chemical modifications for increasing the stability of ribozymes, such as the introduction of an alkyl group at the 5' carbon of a nucleoside or nucleotide sugar. Such modifications can also be used in EGS molecules. An alkyl group refers to a saturated aliphatic hydrocarbon, including straight chain, branch chain, and cyclic alkyl groups. It is preferred that such alkyl groups have 1 to 12 carbons. WO 95/23225 also describes 2'-deoxy-2'-alkylnucleotides which may be present to enhance the stability of oligonucleotides. For example, an oligonucleotide having at the 2'-position on the sugar molecule an alkyl moiety present where the nucleotide is not essential for function will be more stable. WO 95/23225 also describes the use of 3' and/or 5' dihalo-phosphonate substituted nucleotides, for example, 3' and/or 5'-$CF_2$-phosphonate substituted nucleotides.

Methods for Coupling of Macrocycles to Oligonucleotides

As discussed above, the compound to be delivered can be coupled to the porphyrin or other macrocycle ionically. It can also be coupled covalently.

Methods for covalently crosslinking porphyrins to protein, oligonucleotide, and polysaccharide polymers are known. For example, a heme molecule has two pendant carboxyl groups, two pendant alkene groups and four methyl groups. The carboxyl groups can be used to ionically or covalently link a polymer to the heme molecule. The carboxyl groups in a heme molecule can react in an acid-base reaction.with amine groups on a polymer to form an ionic bond. The carboxyl groups can also be reacted with hydroxy groups on a polymer using a multi-valent ion, such as $Ca^{++}$ to effect the coupling. The carboxyl groups in a heme molecule can be reacted with pendant hydroxy, amine, thiol or carboxy groups on a polymer by means known to those skilled in the art of organic synthesis, for example, using a dehydrating agent such as DCC. The resulting products are esters, amides, thioesters and anhydrides, respectively. Representative methods are listed in Larock, "Comprehensive Organic Transformation, VCH, New York, 966–972 (1989), hereby incorporated by reference. The alkene and methyl groups can form radicals, which can be used to covalently link a polymer to the heme molecule. To link the polymer to the heme molecule, the polymer needs to have at least one reactive group that reacts with a carboxyl group, an alkene group or a methyl radical to form an ionic or covalent bond. The pendant alkene groups in a heme molecule can be covalently coupled to a polymer containing alkene groups using a free-radical initiator. To crosslink the polymer and the heme molecule, the polymer must have at least two reactive groups. Alternatively, one can polymerize unsaturated monomers, such as acrylate monomers, in the presence of the heme molecule to form alternating copolymers incorporating the heme unit.

The pendant methyl groups form radicals when subjected to UV or gamma radiation. The methyl groups can be coupled to polymers containing pendant aliphatic carbon-hydrogen, carbon-chlorine or carbon-bromine bonds by subjecting the methyl groups on the heme molecule to UV or gamma radiation in the presence of the polymer.

III. Methods of Use
Methods of Therapeutic Application

The conjugate of compound to be delivered and macrocyle, for example, oligonucleotide-porphyrin conjugates, will preferably be administered systemically, most typically by intravenous or intraperitoneal injection, in an amount effective for delivery of the compound to the targeted cells. Other routes of administration that are useful include topical, transdermal, transmucosal and enteral. Generally, the total amount of the macrocycle-associated compound administered to an individual will be less than the amount of the unassociated compound that must be administered for the same desired or intended effect. The effective amount is also dependent on whether the mode of administration is by a replicon, or vector-driven approach, e.g., a retroviral vector which amplifies the sequence it is carrying, or by a chemically-synthesized oligonucleotide approach. Cells which preferentially bind to porphyrins include hepatocytes, tumor cells and atherosclerotic plaque.

The porphyrin can also be administered directly, not in combination with compound such as oligonucleotide, in an amount effective to inhibit viral replication, as demonstrated by the following examples.

Methods for Diagnostic and Research Applications

Although described primarily with reference to delivery of therapeutics, it will be recognized by those skilled in the art that the same delivery system can be used for laboratory reagents for transfection of cells and in diagnostic assays. For example, the oligonucleotide may be a labeled probe, designed to target cells which contain a receptor or nucleic acid specifically reactive with the probe.

The present invention will be further understood by reference to the following non-limiting examples.

EXAMPLE 1
Binding of Cationic Porphyrin Meso-tetra(N-methyl-4 pyridyl)porphine Tetra Tosylate (TMP) to Nucleic Acids In vitro The following oligonucleotides were used throughout this work. They were synthesised either on a Millipore Expedite DNA synthesiser, or an ABI 392 Synthesiser. Underlining indicates phosphorothioated linkages in oligoribonucleotides, upper case indicated 2' O-methyl substituted ribose moieties and lowercase indicates unmodified ribonucleotides:

I. oligo A: 5' AUGAUAGAAGG UUCGAAUCCUUCACGCCGC (SEQUENCE ID NO 1); oligo B: 5' agcgaugaagguucgaauccuuccaggac (SEQUENCE ID NO 2); oligo C: 5' FL-CUCAAGAAGG UUCGAAUCCUUCGGCUGCCT (SEQUENCE ID NO 3).

A method was developed to determine the degree of binding of nucleic acid to porphyrin that involved passing a labelled nucleic acid: porphyrin complex through a carboxymethyl (CM) ion exchange column. In the absence of porphyrin the nucleic acid passed through the column, while it was retained after binding to the cationic porphyrin. The counts present in the material eluted indicated the amount of nucleic acid unbound.

Carboxy methyl resin (BioGel A) was obtained from BioRad. Columns containing 1 ml CM resin were prepared in Biorad polyprep disposable columns and were washed with 2 ml 150 mM NaCl. Tetra meso(n-methyl 4-pyridyl) porphine (TMP) (mw 1363) was obtained from Porphyrin Products, Inc. (Logan, Utah) and was made up to 15 mg/ml in 150 mM NaCl. 120 $\mu$l volumes of TMP containing 0, 18, 60, 180, 600, 1800 $\mu$g TMP were prepared and incubated with 120 $\mu$l volumes containing 60 $\mu$g of oligo A in 150 mM NaCl and approximately $3\times10^4$ cpm of $^{32}$P-labelled oligo as a radioactive tag. The complexes were incubated for 30 min at room temperature, then each was added to the CM column and unbound oligo eluted with 1 ml 150 mM NaCl. The eluate was counted and percent bound to TMP was calculated.

The data indicate that complete binding of 60 $\mu$g oligo occurred with 60 $\mu$g TMP.

To investigate the interaction of double-stranded plasmid DNA with TMP, a titration range of TMP from 5 $\mu$g to 500 $\mu$g was complexed with 20 $\mu$g 9.5 kbp plasmid containing approximately $3\times10^4$ cpm plasmid, labelled by random-priming using Klenow. Unbound plasmid was eluted from a 1 ml CM column as above. The results demonstrate that low levels of plasmid bind to TMP, in contrast to the situation with the single-stranded short oligoribonucleotide. Only 5 $\mu$g plasmid was bound to 500 $\mu$g TMP. The reason is likely to be a result of the vastly different structure of short single-stranded nucleic acids versus large circular double-stranded plasmids, and may be due to differences in accessibility of phosphate groups. It should be possible to overcome this by using different porphyrins, or by using higher concentrations of TMP.

The interaction of nucleic acids with water soluble porphyrins can easily be followed by measuring the absorbance spectrum of the porphyrin in the range 350–450 nm. Porphyrins have a characteristic Soret peak in this wavelength range. For TMP the Soret peak is found at 421 nm. When nucleic acids are added to the TMP solution the Soret peak shifts gradually to 440 nm for fully saturated porphyrin, and this spectral shift can be used to measure the degree of binding. One hundred and twenty $\mu$l 150 mM NaCl containing 2.4 $\mu$g TMP were added to an equal volume of 150 mM NaCl containing various amounts of oligo A in the range 0.1–10 $\mu$g. Spectra were taken over the range 300–500 nm and the wavelength of the Soret peak plotted against the mass of EGS. The point at which the Soret peak reached 440 nm was taken as the point at which saturation occurred and this was taken as approximately 3 $\mu$g in this experiment.

From the above experiments, titrating oligo with TMP, it was shown that approximately equal masses of porphyrin and oligo interact at saturation. For 1 $\mu$g TMP this calculates to $1/1363\times10^{-6}$ mol=0.73 nmol. For 1 $\mu$g 30 mer oligo this calculates to $1/1000\times10^{-6}$ mol=0.1. For TMP there are four positive charges per molecule therefore 0.73 nmol has 2.92 nmol positive charge. For the oligo there are 29 negative charges per molecule, therefore 0.1 nmol has 2.9 negative charges. The evidence shows that saturation occurs at charge neutralisation and that 4 molecules of oligo interact with 29 molecules of TMP at saturation.

Published work describes an external stacking phenomenon of TMP on oligomeric nucleic acids (Gibbs, et al., Biochem. Biophys. Res. Com. (1988) 157, 350–358), and for the ribonucleic acid: TMP interaction described here the stoichiometry of binding would agree with this kind of model.

The oligoribonucleotide used in the above experiments is a chimaera composed of 23 nucleotides containing 2'O-methyl modifications of the ribose moiety, and the rest of the nucleotides containing phosphorothioated linkage modifications. The influence of the modifications on the interaction of the oligo with TMP was investigated. All-phosphorothioate deoxyribose 30 mers and phosphodiester deoxyribose 30 mers (DNAs) were used in binding experiments giving exactly the same results as the 2'O-methyl versions. Also 50 mer and 100 mer DNA single-stranded oligos were used and the same stoichiometry of binding was observed. Thus it seems that chemical modification of the single stranded oligo has little influence on the nature of the binding of the porphyrin, and this interaction is likely due to the charge interaction between the cationic and anionic components.

The influence on nucleic acid binding of a chelated Fe atom in the tetrapyrrole ring was investigated. Fe TMP behaved no differently than TMP alone. The cationic porphyrin meso-tetra trimethyl anilinium porphine, however behaved differently with approximately 100 $\mu$g porphyrin required to saturate 60 $\mu$g oligo in a column binding assay.

EXAMPLE 2

Protection of Nucleic Acid by TMP.

One function of an effective delivery system is its ability to protect the carried drug. Nucleic acid therapeutics are potentially labile and protection from the effects of serum and cellular nucleases is a requisite for their intact accumulation at an intracellular site of action. From the above experiments it was clear that cationic porphyrins bind to the single-stranded oligos very effectively. An experiment was therefore carried out to determine if this binding increased stability in human serum.

4 $\mu$g all-RNA oligo B containing a small amount of polynucleotide kinase $^{32}$P-labelled oligo B was mixed with an excess of TMP (375 $\mu$g) and a sample taken for time 0 determination. To the oligo:TMP mixture an equal volume of human serum was added (to give a 50% final concentration) and after 30 min and 24 h further samples were taken. Each sample was treated with proteinase K buffer (10 mM Tris pH 8; 5 mM EDTA; 0.5% SDS; 0.5 mg/ml proteinase K) for 10 m at 37° C. Samples were phenol/chloroform extracted, ethanol precipitated and electrophoresed through a 15% polyacrylamide gel.

After 30 min with TMP, over 90% of the RNA remained full-length, while at this timepoint, without the carrier, all of the RNA oligo had degraded. At the 24 h timepoint greater than 75% of the oligo remained full-length when associated with TMP. This data demonstrates that the binding of TMP to the nucleic acid prevents its degradation, perhaps by hindering access of nucleases to the phospodiester backbone.

EXAMPLE 3

Delivery of Nucleic Acids to Cells in Culture by Interaction with TMP

The results of Example 1 demonstrate that nucleic acids interact with the cationic porphyrin TMP. It was next investigated if TMP was capable of delivering bound nucleic acids to cells in culture.

Human hepatoma cells containing four copies of the hepatitis genome (HepG2 2.2.15 cells) (Sells, et al. (1987) Production of hepatitis B virus particles in HepG2 cells transfected with cloned hepatitis B virus DNA. *Proc. Natl. Acad. Sci. USA* 84, 1005–1009) were plated out onto 96-well plates at $10^4$ cells per well, and left for 3 days until approximately 90% confluent. 1, 5 or 10 $\mu$g of oligo A were complexed with 0–300 $\mu$g of TMP in 40 $\mu$l 150 mM NaCl. $^{32}$P-kinased oligo was used to determine binding levels. The complexed oligo was delivered to the cell cultures (6 replicates per variable), samples were removed for measurement of delivered radioactivity cpm and the cultures were returned to a 37° C. incubator for 4 h. Cultures were washed three times with 100 $\mu$l PBS and cells were lysed with SDS lysis buffer for extraction of nucleic acids (0.5% SDS, 10 mM Tris HCl pH 7.4, 10 mM EDTA, 10 mM NaCl, 500 mg/ml proteinase K). Lysates were counted to determine cell-associated radioactivity and nucleic acids were extracted from the lysate by phenol-chloroform treatment and ethanol precipitation. Extracted nuclei acids were electrophoresed through 15% polyacrylamide/urea gels to determine the integrity of the delivered nucleic acids.

The cell binding data are shown in FIG. 1. For each dose of oligo saturation of binding or uptake occurred at 30 $\mu$g TMP. Approximately 50% of the added dose was cell-associated for all oligo doses. A maximum of up to 4–5 $\mu$g of oligo was cell associated with $3\times10^4$ cells. Substantial amounts of the oligos that were dell-associated were full-length. As a comparison of an alternative cationic delivery reagent, the cationic lipid mixture DOTAP:DOPE (dioleyoyltrimethylammonium propane:dioleoyl phosphatidyl ethanolamine 1:1 molar ratio, 5 $\mu$g) (Leventis and Silvius (1990) Interactions of mammalian cells with lipid dispersion containing novel metabolisable cationic amphiphiles. *Biochim. Biophys. Acta* 1023, 124–132) was complexed with 10 $\mu$g, 5 $\mu$g or 1 $\mu$g oligo and delivered as above. 0.97 ($\pm$0.16), 0.62 ($\pm$0.045) and 0.14 ($\pm$0.0065) $\mu$g (n=6) oligo were delivered respectively for the 10, 5 and 1 $\mu$g delivered doses, compared with maximally 4.8, 2.8 and 0.5 $\mu$g for the corresponding amount delivered with TMP.

Figure 2:
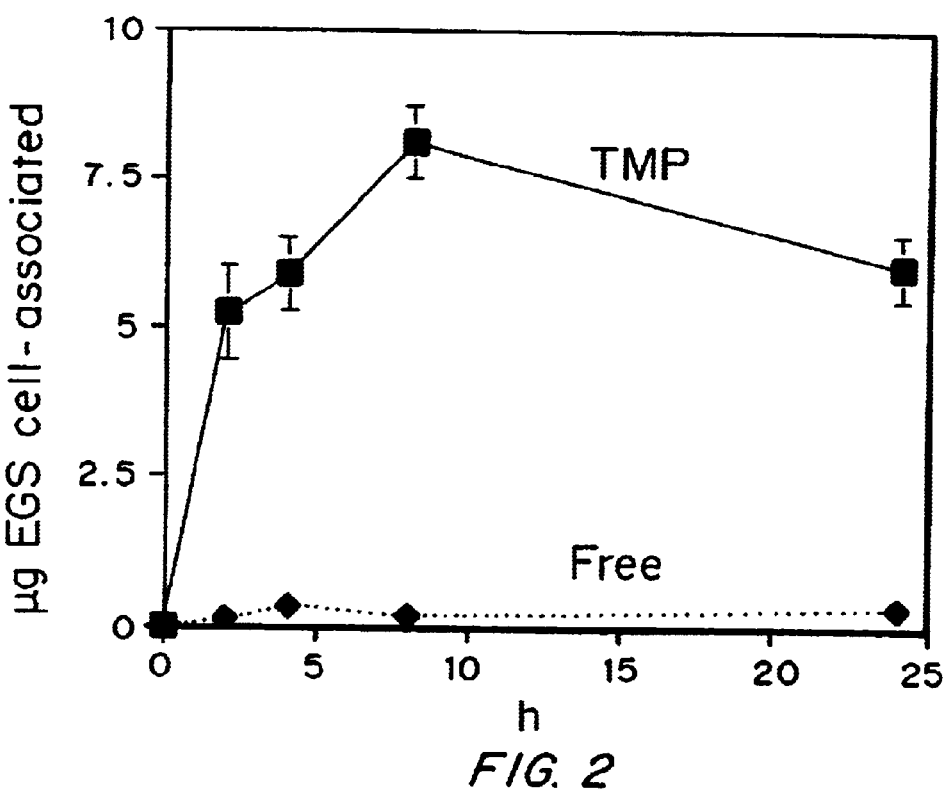
FIG. 2 is a graph of the amount of EGS (micrograms) associated with human hepatoma cells over time (hours) for a complex consisting of 30 μg TMP and 10 μg oligo. Complexes were added to 6 replicate wells in a 96 well plate. A control timecourse was prepared without a delivery vehicle.

A timecourse experiment was carried out to determine the kinetics of binding/uptake of TMP-delivered oligonucleotides to hepatoma cells. In this experiment 30 $\mu$g TMP and 10 $\mu$g oligo A were complexed and added to 6 replicate wells in a 96 well plate. A control timecourse was prepared without a delivery vehicle. Nucleic acids were recovered from one set of wells and were purified and analysed as described above. In this experiment negligble material was cell-associated without a delivery vehicle but greater than 75% of the oligo was cell-associated following TMP delivery at the 8 h timepoint (FIG. 2). After 24 h there was a reduction in the material cell-associated and this may be due to degradation or efflux of the oligo. Substantial amounts of full-length oligo were recoverable from cells throughout the course of this experiment.

EXAMPLE 4

Cellular Localisation of EGSs Delivered by TMP

The above experiments showed that the cationic porphyrin can deliver high levels of short nucleic acids into cells in tissue culture. In the following experiments the intracellular location of the delivered oligo was investigated using two methods, cell fractionation and fluorescence microscopy.

Cell Fractionation

HepG2 2.2.15 cells were seeded at $10^5$ cells per ml into 1 ml wells of a 24 well plate and allowed to grow to 80% confluence. Ten micrograms of oligo A were mixed with various amounts of TMP in 150 mM NaCl, ranging from 10–100 $\mu$g in 100 $\mu$l total. A small amount of kinased oligo A was used to follow the location of the delivered nucleic acid. For comparison, 10 $\mu$g DOTAP:DOPE was complexed with 10 µg oligo A containing radiolabel as above. These complexes were added to the cell monolayers in quadruplicate, a 10 µl sample was taken to determine cpm added, and the cells incubated at 37° C. for the times indicated. After incubation, the cells were washed three times with PBS and the cells from each well lysed with 50 µl sucrose buffer I (0.32 M sucrose, 3 mM $CaCl_2$, 2 mM MgOAc, 0.1 mM EDTA, 10 mM Tris-HCl, pH 8.0, 1 mM DTT, 0.5 mM PMSF, 0.5% (v/v) NP-40) (Dyer, R. B. and Herzog, N. K. 1995, Isolation of intact nuclei for nuclear extract preparation from a fragile B-lymphocyte cell line. *Biotechniques*, 19, 192–195) by gentle pipetting. The lysate was centrifuged in an Eppendorf microfuge at 500 g for 10 min at 4° C. and the cytoplasmic supernatant fraction was transferred to a fresh tube. Pellets (nuclear fraction) and supernatants were counted to determine amounts of oligo in each and samples from each were examined following polyacrylamide gel electrophoresis.

Figure 3A:
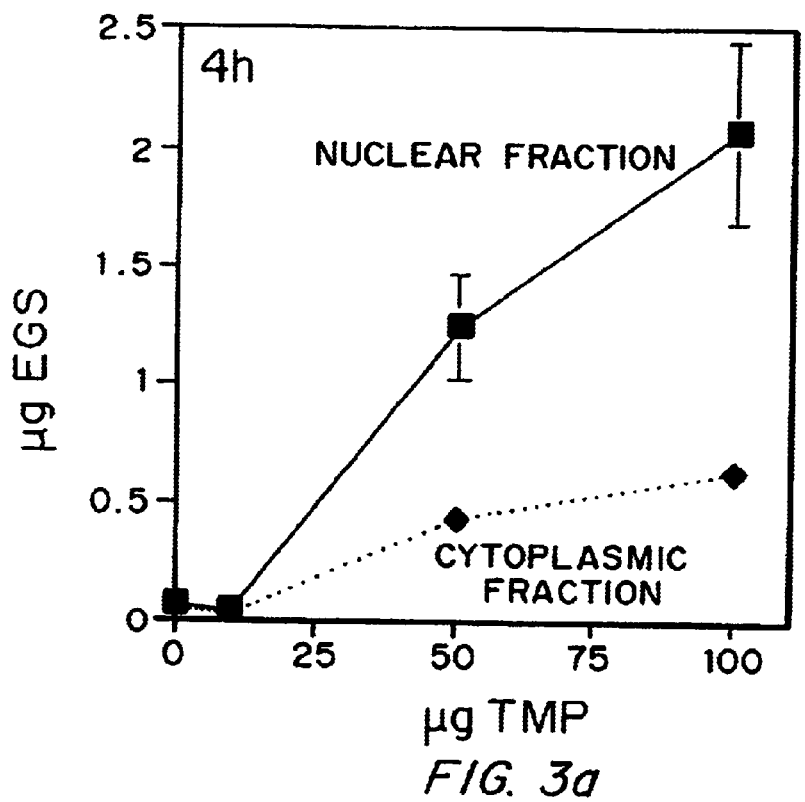
FIGS. 3a and 3b are graphs of the amount of EGS that localised to the nuclear or cytoplasmic fraction of Hep G2 2.15 cells (10–100 micrograms of oligo A mixed with various amounts of TMP (micrograms) in 150 mM NaCl.
Figure 3B:
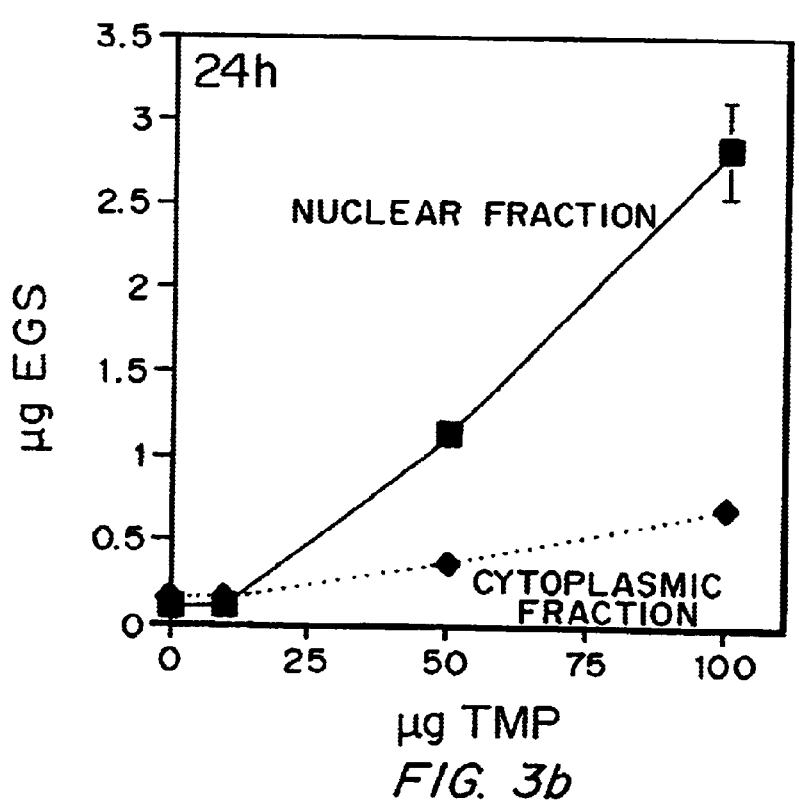

The results of this study are given in FIGS. 3a–b. At 4 h (FIG. 3a) approximately 20% of the added dose is present in the nuclei of HepG2 2.2.15 cells, and this is almost four times the amount present in the cytoplasmic fraction. This result implies that there is a very rapid uptake of the delivered nucleic acid into the nucleus and the very slight increase in nuclear-associated material at 24 h (FIG. 3b) implies that the nuclei have become saturated. The wells contain approximately $10^6$ cells at this degree of confluency thus, by calculation, each nucleus will contain 2 ng EGS, and therefore will contain $1.24 \times 10^8$ molecules. The oligo appears to be predominantly full-length in the nucleus and cytoplasm. As a comparison with the liposome-delivered material at 4 h, 54 ng was nuclear per well and 84 ng remained cytoplasmic, which after 24 h 126 ng was nuclear and 297 ng was cytoplasmic. Thus the distribution of nucleic acid following liposomal delivery was quite different, with the majority of the delivered material being cytoplasmic.

Fluorescence Microscopy

A 30 mer oligo containing a 5' fluorescein isothiocyanate molecule was synthesised, oligo C. Sterile glass coverslips were placed into the wells of 6-well plates and HepG2 2.2.15 cells were seeded into the wells at $5 \times 10^4$ cells/well. 100 µg of the fluorescent oligo was complexed with 100 µg TMP in 150 mM NaCl and delivered to the cells. Also, 100 µg of a non-fluorescent oligo was complexed with 100 µg TMP and delivered to another well as was 100 µg of the fluorescent oligo alone. After 1.5 h and 4 h the coverslips were removed from the wells, dipped five times in PBS to remove excess oligo and were fixed in 4% formaldehyde in PBS. The coverslips were mounted in Slowfade (Molecular Probes, Inc.), and viewed on a Nikon Diaphot fluorescence microscope.

All nuclei of the cells in the TMP-delivered fluorescent oligo cultures appeared brightly fluorescent, with very little fluorescence visible in the cytoplasm. Controls with non-fluorescent oligo showed minimal background red fluorescence, and a low level punctuate cytoplasmic fluorescence was observed with the fluorescent oligo delivered free. In the TMP nuclei small circular regions of less intense fluorescence were observable and these could be nucleoli. The intensity of fluorescence appeared quite uniform throughout the culture. At 4 h the intensity of fluorescence was no greater than at 1.5 h. The results of the fluorescence experiment confirm the data obtained with the cell fractionation study and show clearly that the soluble cationic porphyrins deliver nucleic acids primarily to the nucleus.

EXAMPLE 5

Delivery of Oligos to Other Cell Types

Binding to and uptake of oligos into adherent hepatoma cells was clearly evident from the previous experiments. To investigate delivery to other cell types, the delivery of TMP-complexed oligos to a suspension leukaemia cell line (NB4 cells) containing a chromosome 15:17 translocation was used. NB4 cells were plated out at $10^4$ cells per well of a 96 well plate and left for 5 days. 10 µg oligo A with trace $^{32}$P radiolabeled oligo was complexed with various amounts of TMP (0–300 µg) in 150 mM NaCl and added to the wells in replicates of 6. After 20 h the cells were removed from the wells to another plate and were washed three times with PBS following centrifugation at 2000 rpm 10 min. The NB4 cells were lysed with nucleic acid lysis buffer as above and the cell lysate counted. Material from one well of each TMP concentration was phenol extracted, ethanol precipitated and electrophoresed in a 15% polyacrylamide gel.

Figure 4:
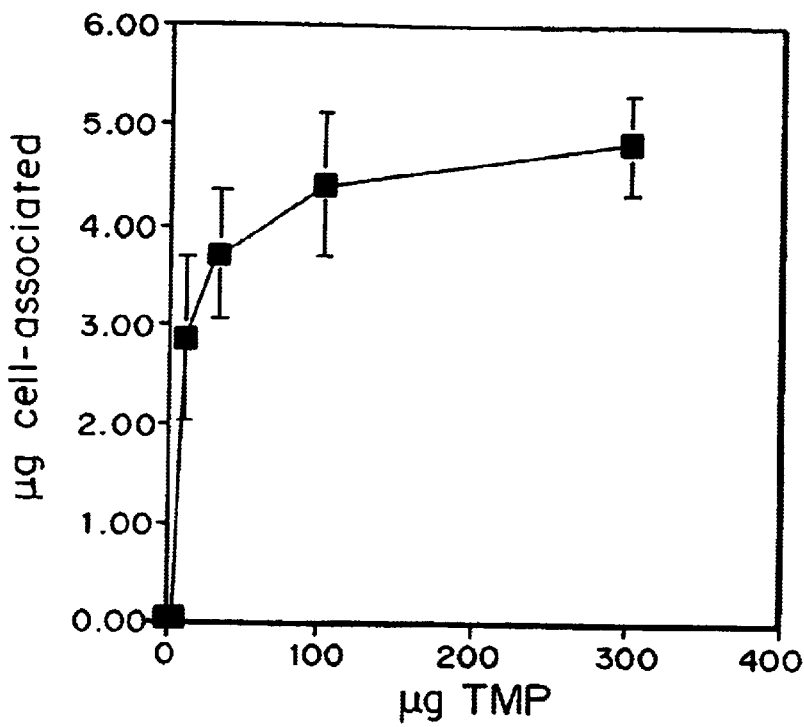

Saturation of binding and/or uptake occurred in these conditions with the suspension cells at approximately 100 µg TMP (FIG. 4), slightly higher than for the adherent cells. In this experiment greater than 50% of the added dose became cell-associated after 20 h, similar to previous experiments. Extracted nucleic acids contained substantially full-length oligo.

EXAMPLE 6

Influence of Serum on TMP Delivery of EGS to HepG2 2.2.15 Cells

Porphyrins are usually bound to carrier serum proteins in the circulation for transport to sites of metabolism (Smith and Morgan (1985) Hemopexin-mediated heme transport to the liver. Evidence for a heme binding protein in liver plasma membranes. *J. Biol. Chem.* 260, 8325; Sinclair, et al. (1988) Effect of serum proteins on heme uptake and metabolism in primary cultures of liver cells. *Biochem. J.* 256, 159) and porphyrin:carrier protein complexes may be taken up via hepatocyte receptors in preference to free porphyrin. In this experiment the influence of different serum concentrations on TMP delivery of complexed oligo to hepatoma cells was investigated, and compared with lipid-mediated delivery, and free delivery under the same conditions.

Ninety-six well plates were set up as described above and allowed to grow until 80% confluence. Six replicate wells for each variable were washed twice with PBS. OPTI MEM (0 serum), 4% FCS in RPMI or 10% FCS in RPMI was added to the appropriate wells.

Thirty µg TMP or 5 µg DOTAP:DOPE were complexed with 5 µg oligo A in 150 mM NaCl, and free oligo was prepared in 150 mM NaCl. Oligo A was radiolabelled as above. These complexes were added to the wells (in replicates of 6) and after 4 h and 24 h the monolayers were washed 3 times with PBS. Cells were lysed as above and radioactivity counted.

Figure 5A:
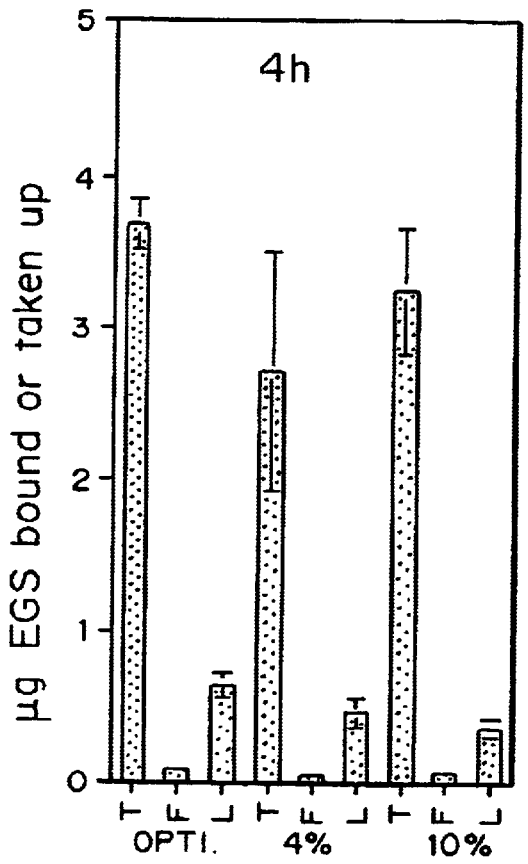
FIGS. 5a and 5b are graphs of the amount of EGS bound or taken up (micrograms) delivered with TMP for OPTI MEM (no serum), 4% and 10% serum at 4 h (FIG. 5a) and 24 h (FIG. 5b).
Figure 5B:
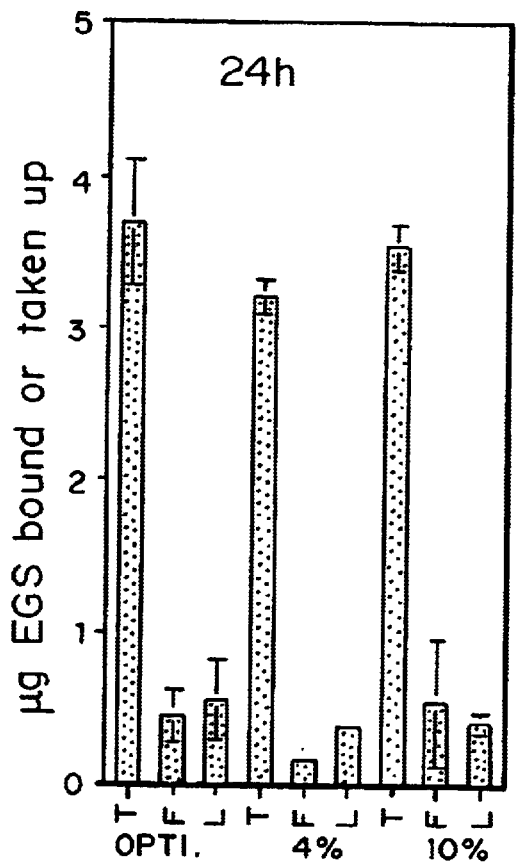

A high proportion of the material delivered with TMP became cell-associated in this experiment (approximately 50–70%) while lipid-delivered and free oligo cell-associated to significantly lower levels (FIGS. 5a and 5b). This confirmed all of the earlier findings. The absence of serum does not reduce TMP-mediated delivery, in fact a slight enhancement is seen in the OPTI MEM wells. There appears little difference between 4% and 10% serum, although 10% serum brings about slightly higher binding or uptake of oligo at both 4 h (FIG. 5a) and 24 h (FIG. 5b). There is little increase in cell association with all serum levels from 4 h to 24 h, again in agreement with previous findings.

EXAMPLE 7

Influence of Different Water-Soluble Cationic Porphyrins on Oligonucleotide Delivery HepG2 2.2.15 cells were set up in 96 well plates as above. Concentration ranges of TMP, Fe-chelated TMP and meso tetra(trimethyl anilinium)porphine (TMA), from 0–300 µg, were complexed in hexatuplicate with 5 µg oligo A, labelled as above. Complexes were added to the cultures and incubated at 37° C. for 4 h. The monolayers were washed three times with PBS and cells were lysed and counted as previously described.

Figure 6:
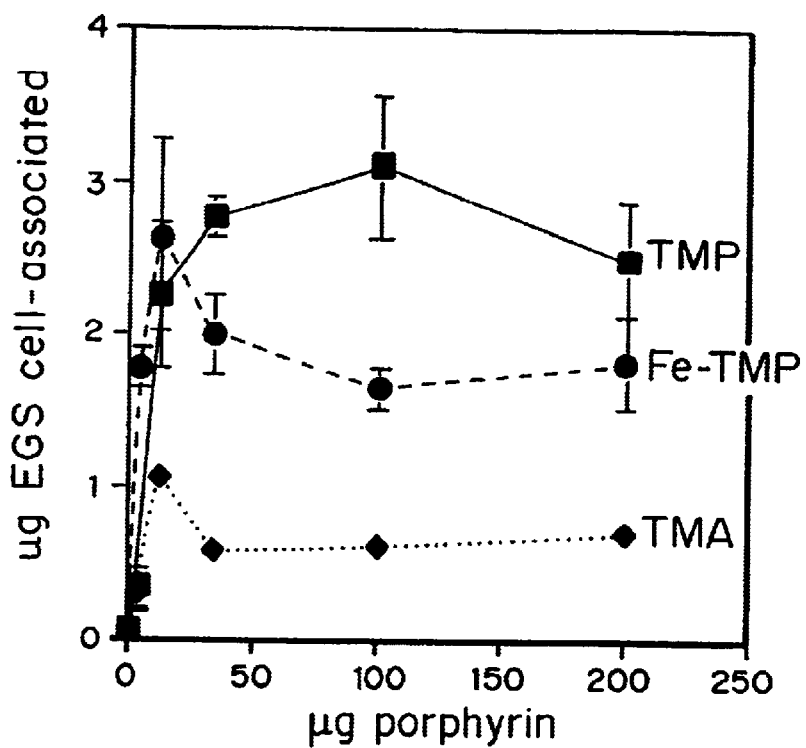
FIG. 6 is a graph of the amount of EGS cell-associated (micrograms) for different amounts of porphyrin (between 0 and 200 micrograms) for TMP, Fe-TMP and meso-tetra trimethyl anilinium porphine.

The results of this experiment are given in FIG. 6. The presence of Fe in the tetrapyrrole ring does not affect cellular delivery by TMP up to a level of 30 µg. At porphyrin levels greater than this, the non Fe chelated version delivers more associated nucleic acid, and the amount delivered with Fe-TMP is reduced from the maximum at 30 µg with increasing porphyrin concentration. Oligo delivered by Fe TMP remains predominantly full-length within cells. TMA is able to deliver oligo also to relatively high levels, however the amount is never as great as the TMP analogues. Again, as with Fe TMP, 11 µg of TMA mediates maximal nucleic acid uptake.

EXAMPLE 8

Accumulation of TMP-delivered Oligoribonucleotide in the Liver

An internally-labelled Oligo A was prepared by kinasing a component oligo with $^{33}$P ATP and ligating this shorter oligo to another short component cold oligo to form the full-length version. This oligo was used to seed cold Oligo A. 100 µg Oligo was complexed with 0, 50, 100, 200 µg TMP in duplicate and injected into the tail veins of 9 week old male CD1 balb-c mice. After 2 h and 24 h the mice were killed by cervical dislocation, weighed and their livers removed. Livers were weighed, homogenized and a small sample counted by liquid scintillation counting.

Figure 7A:
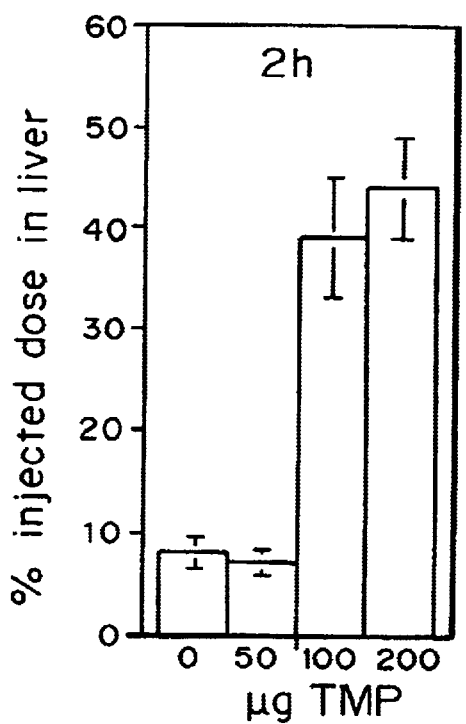
FIGS. 7a and 7b are graphs of the percent injected dose in liver for different amounts of TMP (micrograms) at 2 h (FIG. 7a) and 24 h (FIG. 7b).
Figure 7B:
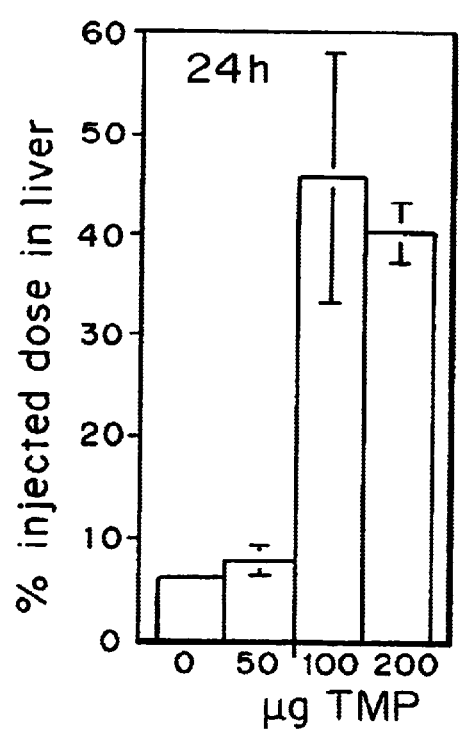
Figure 8A:
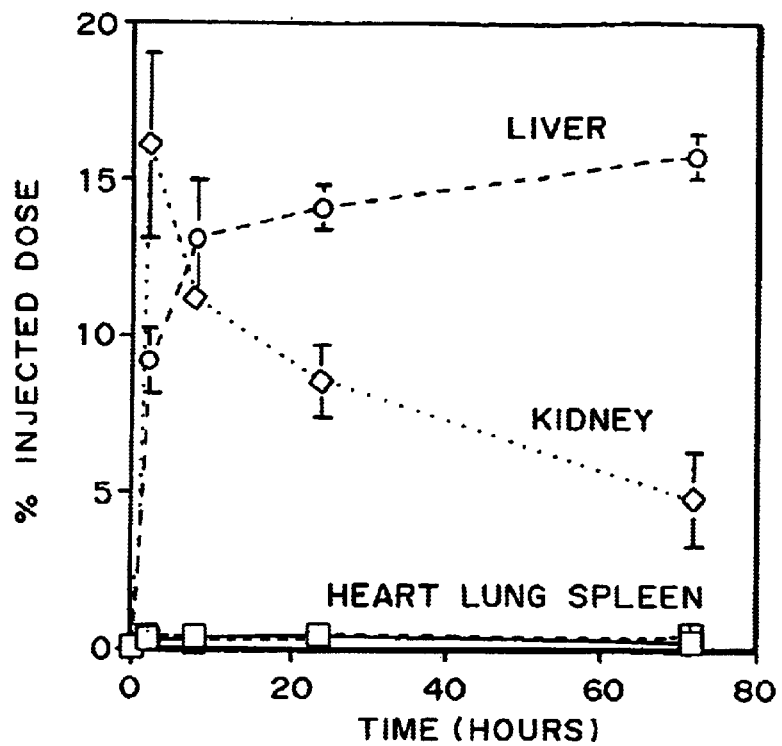
FIGS. 8a and 8b are graphs of percent injected dose over time (h) for 100 micrograms TMP:100 micrograms EGS per mouse (FIG. 8a) and 20 micrograms TMP:100 micrograms EGS per mouse (FIG. 8b).
Figure 8B:
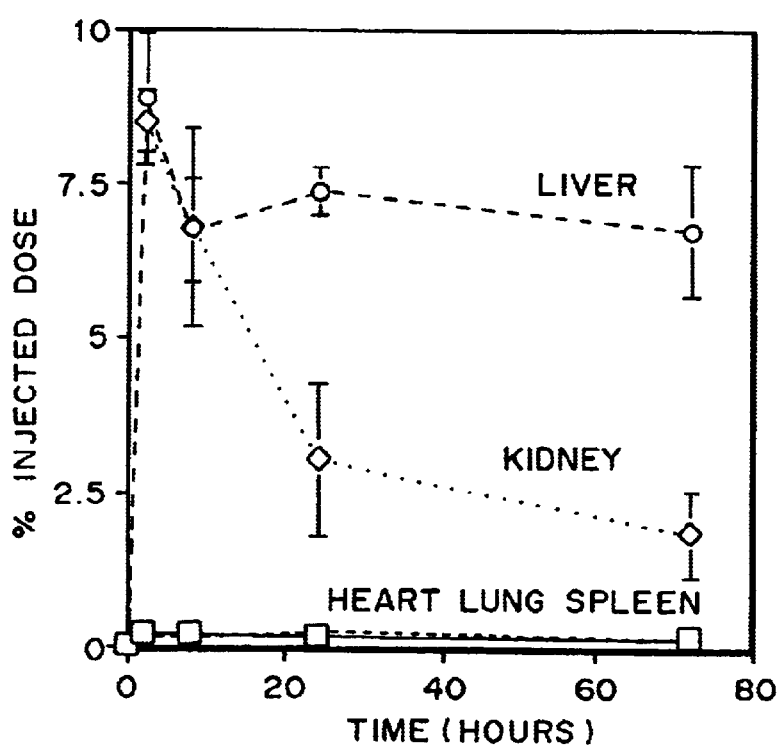
Figure 9:
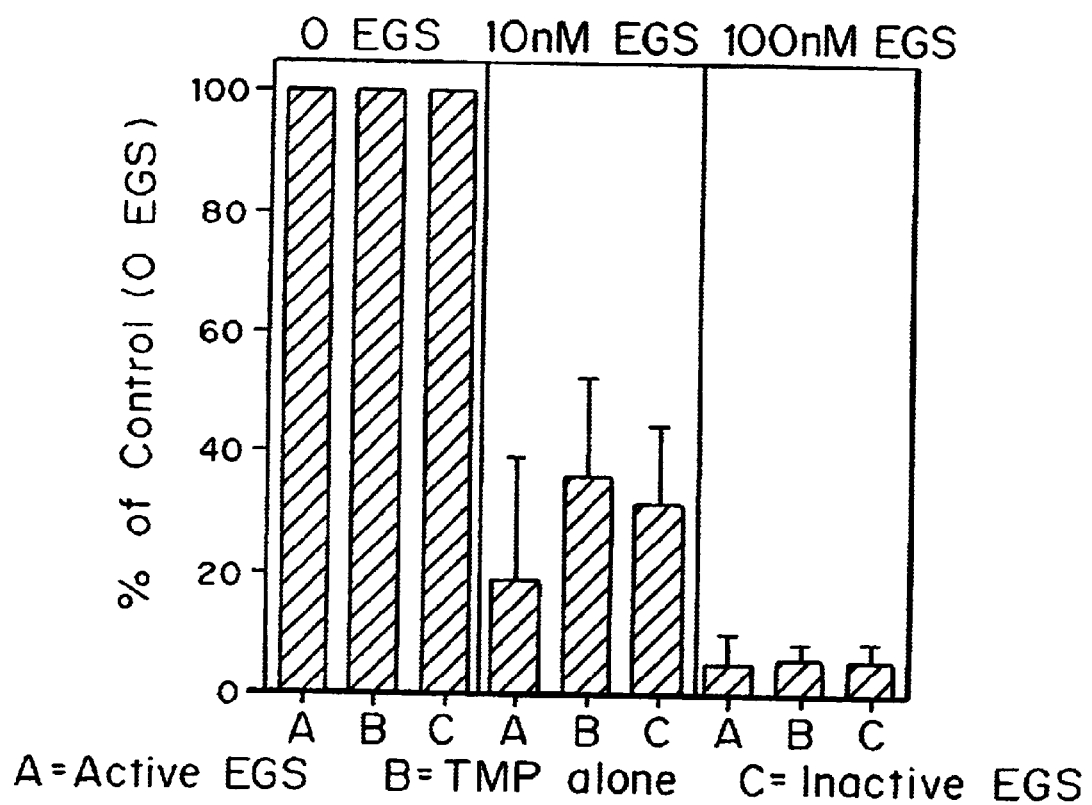
FIG. 9 is a graph of percent of Control (no EGS) for active EGS (A), TMP alone (B), and inactive EGS (C), at 0 EGS (negative control), 10 nM EGS and 100 nM EGS.

The results are given in FIGS. 7a and 7b. When 100 or 200 µg TMP were used to deliver 100 µg oligo, approximately 40% of the injected dose rapidly localised to the liver. This level of delivered oligo persisted for 24 h. This level of TMP appeared to be well tolerated by the mice. The results show that this soluble porphyrin delivery vehicle is effective for hepatic delivery.

EXAMPLE 9

In situ Hybridisation Demonstrating Intrahepatic Distribution of TMP-delivered EGS 200 µg 30 mer EGS oligo A was complexed with 100 µg TMP in 200 µl 150 mM NaCl and injected into the tail veins of duplicate adult male CD1 mice as described in Example 8. Free EGS (800 µg/mouse) in the absence of TMP was injected as a control. After 8 h and 24 h mice were sacrificed and their livers quickly immersed in OCT medium (Tissue-Tek) and frozen in liquid $N_2$. Thin sections were cut and sections were mounted on glass slides. Localisation of EGS in the liver section was determined by hybridisation of a $^{33}$P-labelled antisense oligonucleotide complementary to the EGS sequence, and overlaying with a photographic emulsion. Background hybridisation was determined using a $^{33}$P-labelled oligo with the same sequence as the EGS.

The prints show silver grains located throughout the liver in high concentration. There is evidence of low level Kupffer cell uptake in contrast to that seen with the cationic liposomes used for delivery of oligonucleotides. There is substantial EGS present in all hepatocytes, and silver grains are present (possibly more concentrated) in the nuclei of the hepatocytes (the darker rounded structures). Prints from the same livers but hybridised with the sense probe show background-level signal. Comparisons were made with a print of a section of the liver from the mouse injected with the free EGS and at a 24 h timepoint of a TMP:EGS mouse liver, hybridised with the antisense strand. The level of signal is reduced after 24 h and may be due to metabolism of the EGS within the hepatocytes. There is, however, specific signal over background indicating persistence of full-length material.

EXAMPLE 10

Biodistribution of TMP-delivered EGS

A trace amount of (30 mer) EGS oligo A was labelled internally with $^{33}$P and used to spike cold EGS. Either (a) 100 µg EGS was complexed with 100 µg TMP per mouse, or (b) 100 µg EGS was complexed with 20 µg TMP per mouse and each complex was injected into the tail veins of adult male 6 week old CD1 mice. At times 2 h, 8 h, 24 h and 72 h three mice were sacrificed per treatment and the liver, kidney, heart, spleen, lungs, fat and blood was removed. The organs were weighed, homogenised and an aliquot counted. 10 µl serum was also counted. Data were expressed as percentage of the injected dose per organ.

The results show that for each injected dose there was a rapid initial peak in the kidney which declined over 72 h. This indicates that there is significant clearance of the EGS via the kidney. There was a rapid accumulation of EGS in the liver at 2 h and the hepatic levels declined slightly over time with the lower TMP dose, but gradually increased with the higher TMP dose. Reproducibility was very good, as indicated by the standard deviation (sd) bars. With the higher TMP level, delivering the same amount of EGS, there was approximately a two-fold enhancement spleen, fat and serum were negligible. No liver toxicity was detected.

EXAMPLE 11

Anti HBV Activity of EGS:TMP Complexes in Cell Culture

The human hepatoma cell line HepG2 2.2.15 containing four copies of the HBV genome was used in this study. Cells were plated out ($2\times10^4$/well) into 96 well plates and left for 5 days until confluent. TMP was complexed with active EGS 203B8, inactive EGS A50 [CUC AAGAAGG uucgaau CCUUCGGC UGCC] (where underlining indicates phosphorylation) or without EGS in 150 mM NaCl at the optimal charge ratio determined in the examples above and diluted in 150 mM NaCl to give a concentration range of 3 µM–10 nM EGS (this corresponded to a concentration range of between 21 µM and 71 nM TMP). The various dilutions were added to the cell monolayers (6 replicates per concentration). Daily treatments were carried out for 5 days changing the medium each day. After the fifth day cell culture supernatant was removed and assayed for extracellular HBV DNA levels by dot-blot using the method of Korba B. E. and Gerin J. L. (Use of a standardized cell culture assay to assess activities of nucleoside analogs against Hepatitis B virus replication. (1992) *Antiviral Research* 19, 55–70).

The results show no toxicity at concentrations less than 700 nM TMP: 100 nM EGS. At concentrations above this the complexes gradually became toxic (35–77% of controls at 2100 nM TMP, and 7–12% of controls at 21 µM TMP). Thus specific antiviral effect of the complex can be assessed at less than 100 nM EGS. At 100 nM EGS all three treatments reduced HBV DNA levels to essentially background, indicating that the TMP is highly antiviral at this concentration. At 10 nM EGS however, there is an enhanced antiviral effect in the presence of the active EGS (perhaps a 50% reduction from the inactive EGS and the TMP alone).

EXAMPLE 12

Demonstration of Anti-HBV Activity in the Nanomolar Range with No Toxicity

A number of EGS were tested under the auspices of the NIH antiviral testing program. TMP-EGSs were tested for anti-hepatitis B viral activity in Hep2 cells over concentration ranges of between 3 and 300 nM.

The TMP-complexed EGSs tested were:

203B7 G̲A̲UGAUAGAAGGU̲U̲C̲G̲A̲A̲
    UCCUUCACGCC̲G̲C̲     (SEQUENCE ID NO 4)

203B8 A̲G̲AUGAUAGAAGGUUCGAA
    UCCUUCACGCC̲G̲C̲     (SEQUENCE ID NO 5)

203B9 A̲A̲GAUGAUAGAAGGU̲U̲C̲G̲A̲A̲U̲
    CCUUCACGCC̲G̲C̲     (SEQUENCE ID NO 6)

203BT A̲U̲GAUAGAAGGU̲U̲C̲G̲A̲A̲UCCUUCACGCCG̲C̲ 3'-3T
    (SEQUENCE ID NO 7)

A50 control CUCAAGAAGGU̲U̲C̲G̲A̲A̲U̲
    CCUUCGGCUGCC     (SEQUENCE ID NO 8)

Underlining indicates phosphorothioated linkages. The rest of the nucleosides are 2' o-methyl substituted. A50 is a non-specific EGS directed at the APL fusion mRNA.

The $EC_{50}$s were in the range of less than 10 nM range, which is approximately 10 to 20 times more effective than the nucleoside analog 3TC which is the most potent recognized anti-HBV drug, in the same system.

Modifications and variations of the a delivery system consisting of postively charged macrocycles such as porphyrins for negatively compounds such as oligonucleotides will be obvious to those skilled in the art from the foregoing detailed description and are intended to come within the scope of the appended claims.

We claim:

1. A method for delivering a compound having a net negative charge to cells comprising
   mixing a compound having a net negative charge with a macrocycle having a net positive charge in an amount effective to enhance delivery of the compound to the cells binding the macrocycle, wherein the macrocycle ionically binds to the compound; and
   delivering the mixture to the cells.

2. The method of claim 1 wherein the compound is selected from the group consisting of proteins, peptides, oligonucleotides, biologically active synthetic organic molecules, polysaccharides, and diagnostic reagents, wherein the compound has a net negative charge at physiological pH.

3. The method of claim 2 wherein the compound is an oligonucleotide.

4. The method of claim 3 wherein the oligonucleotide is selected from the group consisting of antisense nucleic acid molecules, ribozymes, external guide sequences for RNase P, aptamers, triplex molecules, genes, viral vectors, plasmids, and protein encoding sequences.

5. The method of claim 1 wherein the macrocycle is a porphyrin.

6. The method of claim 1 wherein the porphyrin is selected from the group consisting of natural porphyrins, natural phthalocyanins, synthetic porphyrins, synthetic phthalocyanins, and conjugates thereof.

7. The method of claim 1 wherein the compound is an oligonucleotide and the macrocycle is a porphyrin further comprising mixing the porphyrin and oligonucleotide in a ratio resulting in all of the oligonucleotide binding to the porphyrin.

8. The method of claim 7 wherein the porphyrin has antiviral activity.

9. The method of claim 8 wherein the porphyrin has anti-hepatitis B activity.

10. The method of claim 9 wherein the porphyrin is tetra meso(n-methyl 4-pyridyl)porphine (TMP).

11. The method of claim 1 wherein the compound has anti-viral activity.

12. The method of claim 11 wherein the compound is an oligonucleotide targeted to viral nucleic acid.

13. The method of claim 12 wherein the viral nucleic acid is hepatitis viral nucleic acid.

14. A method for inhibiting hepatitis B infection of cells comprising
   administering to the cells an effective amount of a porphyrin to inhibit replication of hepatitis B in the cells.

15. The method of claim 14 wherein the porphyrin is selected from the group consisting of natural porphyrins, natural phthalocyanins, synthetic porphyrins, synthetic phthalocyanins, and conjugates thereof.

16. The method of claim 15 wherein the porphyrin is a synthetic porphyrin.

17. The method of claim 16 wherein the porphyrin is tetra meso(n-methyl 4-pyridyl)porphine (TMP).

18. The method of claim 14 wherein the porphyrin is administered to a patient in need of treatment thereof.

19. A composition for delivering a compound having a net negative charge to cells comprising
   a) a compound having a net negative charge ionically bound to a macrocycle having a net positive charge selected from the group consisting of natural porphyrins, natural phthalocyanins, synthetic porphyrins, synthetic phthalocyanins, and conjugates thereof, in an amount effective to enhance delivery of the compound to cells preferentially binding the macrocycle, and
   b) a pharmaceutically acceptable carrier for pharmaceutical administration.

20. The composition of claim 19 wherein the compound is selected from the group consisting of proteins, peptides, oligonucleotides, biologically active synthetic organic molecules, polysaccharides, and diagnostic reagents, wherein the compound has a net negative charge at physiological pH.

21. The composition of claim 20 wherein the compound is an oligonucleotide.

22. The composition of claim 21 wherein the oligonucleotide is selected from the group consisting of antisense nucleic acid molecules, ribozymes, external guide sequences for RNase P, aptamers, triplex molecules, genes, viral vectors, plasmids, and protein encoding sequences.

23. The composition of claim 19 wherein the macrocycle is a porphyrin selected from the group consisting of natural porphyrins, natural phthalocyanins, synthetic porphyrins, synthetic phthalocyanins, and conjugates thereof.

24. The composition of claim 19 wherein the compound is an oligonucleotide and the macrocycle is a porphyrin further comprising mixing the porphyrin and oligonucleotide in a ratio resulting in all of the oligonucleotide binding to the porphyrin.

25. The composition of claim 23 wherein the porphyrin has antiviral activity.

26. The composition of claim 25 wherein the porphyrin has anti-hepatitis B activity.

27. The composition of claim 26 wherein the porphyrin is tetra meso(n-methyl 4-pyridyl)porphine (TMP).

28. The composition of claim 26 wherein the porphyrin is bound to oligonucleotide to be delivered.

29. The composition of claim 28 wherein the oligonucleotide is an external guide sequence for RNase P.

30. The composition of claim 19 wherein the compound is a protein or a peptide comprising L-amino acids or D-amino acids with a net negative charge.

31. The method of claim 1, wherein the compound is internalized inside the cells after it is delivered to the cells, and wherein the compound dissociates from the macrocycle after the compound is internalized inside the cells.

* * * * *